United States Patent [19]

Chandrasegaran

[11] Patent Number: 5,436,150
[45] Date of Patent: Jul. 25, 1995

[54] FUNCTIONAL DOMAINS IN FLAVOBACTERIUM OKEANOKOITIES (FOKI) RESTRICTION ENDONUCLEASE

[75] Inventor: Srinivasan Chandrasegaran, Baltimore, Md.

[73] Assignee: The Johns Hopkins University, Baltimore, Md.

[21] Appl. No.: 126,564

[22] Filed: Sep. 27, 1993

Related U.S. Application Data

[63] Continuation-in-part of Ser. No. 17,493, Feb. 12, 1993, abandoned, which is a continuation-in-part of Ser. No. 862,831, Apr. 3, 1992, Pat. No. 5,356,802.

[51] Int. Cl.$^6$ .................... C12N 9/14; C12N 15/55
[52] U.S. Cl. .................. 435/199; 435/252.33; 435/69.7; 536/23.2
[58] Field of Search ............. 435/199, 193, 252.33, 435/69.2; 536/23.2; 935/47

[56] References Cited

PUBLICATIONS

Blocklage, H., et al., (1991) Nucl. Acids Res. 19(5), 1007–1013.

Kita, K., et al., (1992) Nucl. Acids Res., 20(16), 4167–4172.

Sigma Catalog (1986), pp. 828, 832, 833.

*Primary Examiner*—Charles L. Patterson, Jr.
*Attorney, Agent, or Firm*—Cushman, Darby & Cushman

[57] ABSTRACT

The present inventors have identified the recognition and cleavage domains of the FokI restriction endonuclease. Accordingly, the present invention relates to DNA segments encoding the recognition and cleavage domains of the FokI restriction endonuclease, respectively. The 41 kDa N-terminal fragment constitutes the FokI recognition domain while the 25 kDa C-terminal fragment constitutes the FokI cleavage nuclease domain. The present invention also relates to hybrid restriction enzymes comprising the nuclease domain of the FokI restriction endonuclease linked to a recognition domain of another enzyme. One such hybrid restriction enzyme is Ubx-$F_N$. This enzyme contains the homeo domain of Ubx linked to the cleavage or nuclease domain of FokI. Additionally, the present invention relates to the construction of two insertion mutants of FokI endonuclease.

21 Claims, 30 Drawing Sheets

FIG. 1

FokIM

5' primer

```
           NcoI           7-bp spacer
5' TA  CCATGG  AGGT   TTAAAAT  ATG  AGA  TTT  ATT  GGC  AGC
              RBS              Met  Arg  Phe  Ile  Gly  Ser
```

3' primer

```
              18-bp complement           NcoI
3' ACT ACG ACA CAG TAA ATT AAG   GGTACC  ATA  5'
```

FokIR

5' primer

```
      BamHI     RBS     7-bp spacer
5' TA  GGATCC  GGAGGT  TTAAAAT  ATG  GTT  TCT  AAA  ATA  AGA  ACT
                                Met  Val  Ser  Lys  Ile  Arg  Thr
```

3' primer

```
          Complementary Strand                BamHI
3' TTA  TTG  CCG  CTC  TAT  TTG  AAA  ATT  ACT  CCTAGG  AT  5'
   Asn  Asn  Gly  Glu  Ile  Asn  Phe
```

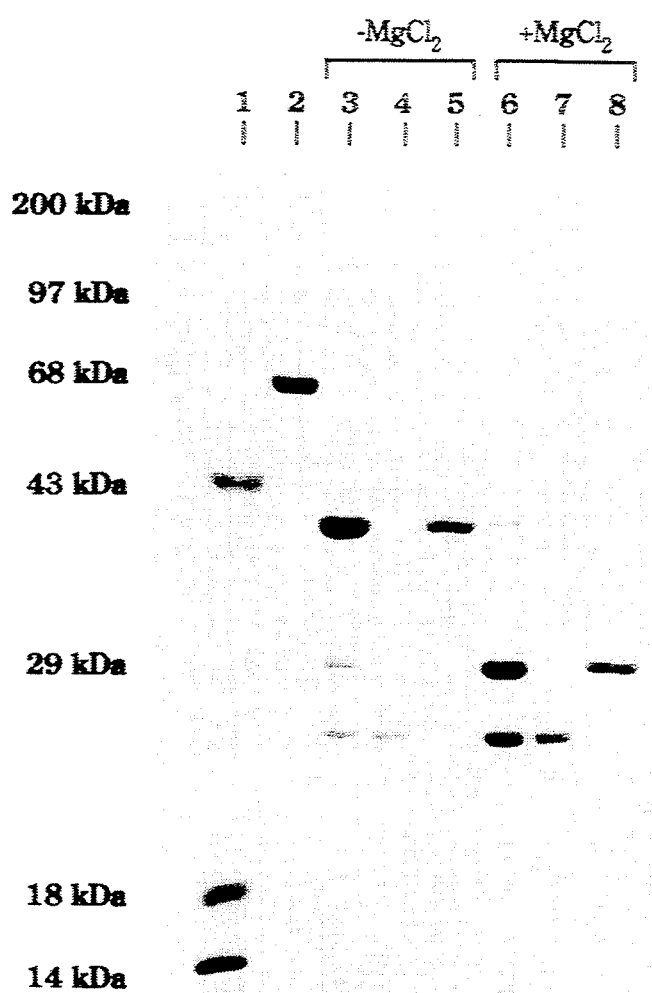

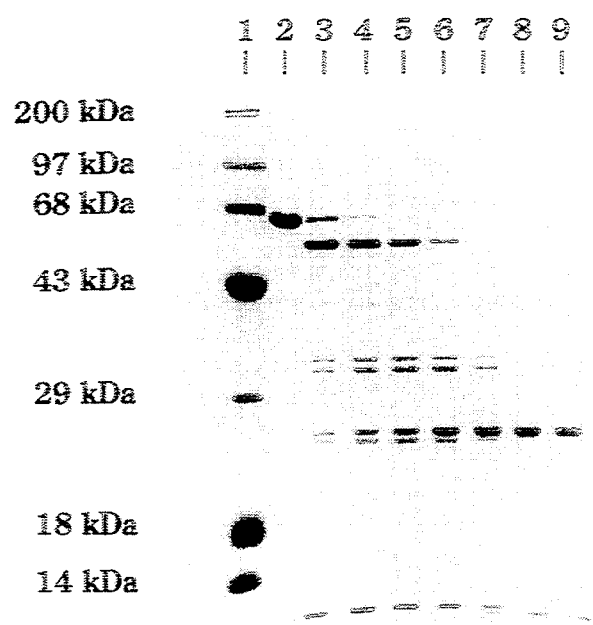

FokI endonuclease

```
MVSKIRTFGWVQNPGKFENLKRVVQVFDRNSKVHNEVKNIKIPTLVKESKIQKELVAIMNQHDLIYTYKELVGTGTSIR
ss.ss.ssss.....hhhhhhhhhh........sssssss..........hhhhhhhhhhh....sssssssssssss SEAPCDAIIQATIADQGNKKGYIDNWSSDGFLRWAHALGFIEYINKSDSFVITDVGLAYSKSADGSAIEKEILIEAISS
....hhhhhhhh.................hhhhhhhhhh.........sssssss..........hhhhhhhhhh..

YPPAIRILTLLEDGQHLTKFDLGKNLGFSGESGFTSLPEGILLDTLANAMPKDKGEIRNNWEGSSDKYARMIGGWLDKL
...sssshhhh...............sss....hhhhhhhhhh..........hhhh....hhhh..hhhh GLVKQGKKEFIIPTLGKPDNKEFISHAFKITGEGLKVLRRAKGSTKFTRVPKRVYWEMLATNLTDKEYVRTRRALILEI
hhhhhh...sss.........hhhhsssss......hhhhhhhhhh....hhhhsssshhhhhhh LIKAGSLKIEQIQDNLKKLGFDEVIETIENDIKGLINTGIFIEIKGRFYQLKDHILQFVIPNRGVTKQLVKSELEEKKS
hhhh..hhhhhhhhhhhhhhhhhhhhhhh...sssssssssssssssssss.........hhhhhhhhhhhhh ELRHKLKYVPHEYIELIEIARNSTQDRILEMKVMEFFMKVYGYRGKHLGGSRKPDGAIYTVGSPIDYGVIVDTKAYSGG
hhhhhh......hhhhhhhhhh.hhhhhhhhhhhhhhhhhhh............ssss.'...ssss........

YNLPIGQADEMQRYVEENQTRNKHINPNEWWKVYPSSVTEEFKFLFVSGHFKGNYKAQLTRLNHITNCNGAVLSVEELLI
.............hhhhhhhhh........hhhsss....sssssss....hhhhhhhhhhhh...hhhhhhhh GGEMIKAGTLTLEEVRRKFNNGEINF
hhhhhh.hhhhhhhhhh........
```

FIG. 10

*fokIR* nt sequence

```
          K   Q   L   V   K   S   E   L   E   E   K
5'- ..... AAG CAA CTA GTC AAA AGT GAA CTG GAG GAG AAG ....... -3'
                  ─────
                   SpeI
```

5' primers:

oligonucleotide for 4-codon insertion

```
      L   V   K   S   E   L   K   S   E   L   E   E   K
5'- GGA CTA GTC AAA TCT GAA CTT AAA AGT GAA CTG GAG GAG AAG -3'
        ─────                    ──────────────────────────
         SpeI                         21-bp complement
``` oligonucleotide for 7-codon insertion

```
      L   V   K   S   E   L   E   E   K   K   S   E   L   E   E   K
5'- GGA CTA GTC AAA TCT GAA CTT GAG GAG AAG AAA AGT GAA CTG GAG GAG AAG -3'
        ─────                                ──────────────────────────
         SpeI                                     21-bp complement
```

3' primer:

```
     N    F   Ter  Ter   BamHI
3'- TTG AAA ATT ACT CCTAGGGGCCCCT -5'
                        ─────
                         XmaI
```

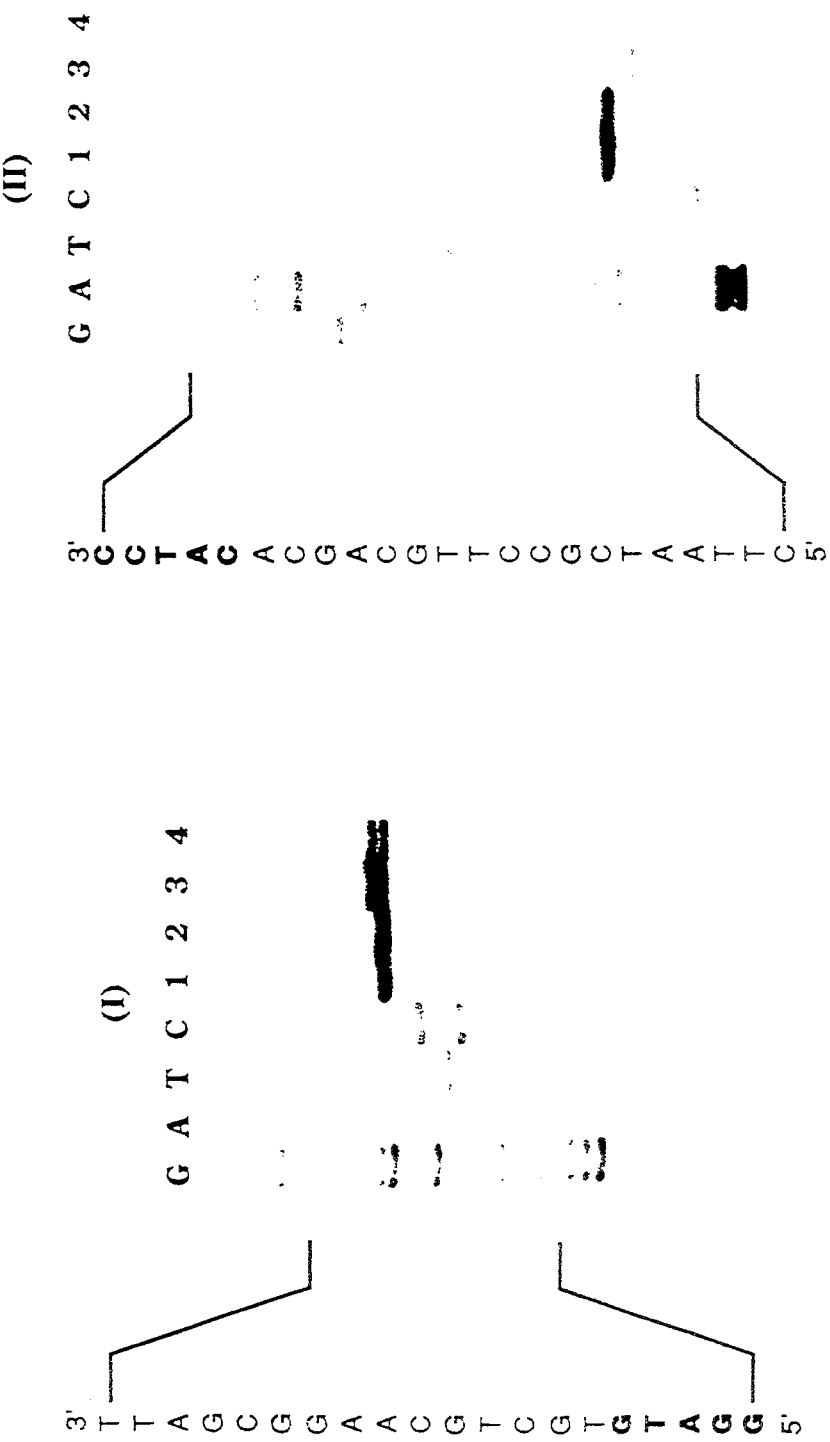

FIG. 15A (A) wild-type *Fok*I

5'- GGATGNNNNNNNNNNNNNNNNN -3'
3'- CCTACNNNNNNNNNNNNNNNNN -5'

(B) 4-codon insertion mutant (C) 7-codon insertion mutant

FIG. 17A

Ubx

```
                PstI
5'-primer:  5' - TAC CTGCAG C GGAGGT TTAAAAT ATG CGA AGA CGC GGC CGA - 3'
                                              Met Arg Arg Arg Gly Arg SpeI
3'-primer:  3' - T TAC TTC GAC TTC CTC TAG GTT GAT CAGAT - 5'
                  Met Lys Leu Lys Glu Ile Gln Leu
```

Ubx-FN

```
                 NdeI
5'-primer:  5' - CCA CGG CAT ATG CGA AGA CGC GGC CGA - 3'
                         Met Arg Arg Arg Gly Arg BamHi
3'-primer:  3' - TTA TTG CCG CTC TAT TTG AAA ATT ACT CCTAGG AT - 5'
                 Asn Asn Gly Glu Ile Asn Phe
```

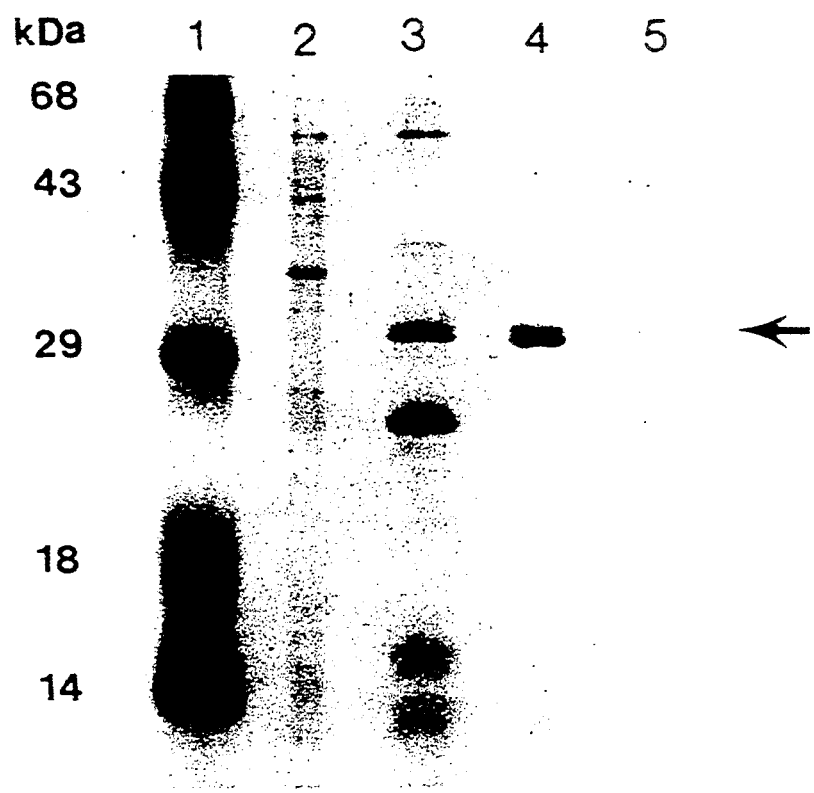

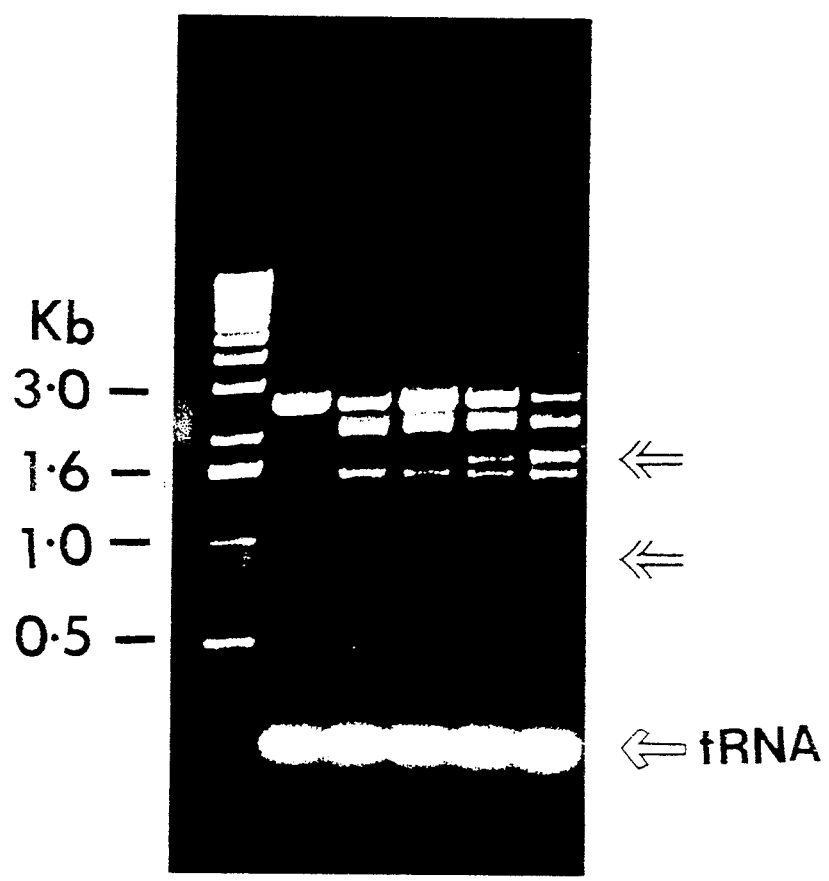

5'— CTCTAGAGGATCCCCGCGCTTAATGGTTTTGC —3'
3'— GAGATCTCCTAGGGGCGCGAATTACCAAAACG —5'

FUNCTIONAL DOMAINS IN FLAVOBACTERIUM OKEANOKOITIES (FOKI) RESTRICTION ENDONUCLEASE

The subject application is a Continuation-In-Part of U.S. patent application Ser. No. 08/017,493, filed on Feb. 12, 1993, now abandoned, and is, in turn, a Continuation-In-Part of U.S. patent application Ser. No. 07/862,831, filed on Apr. 3, 1992, now U.S. Pat. No. 5,350,802. Both CIP applications are hereby incorporated in their entirety by reference.

The invention disclosed and claimed herein was made under grant number GM42140 awarded by the National Institutes of Health.

BACKGROUND OF THE INVENTION

1. Field of the Invention

The present invention relates to the FokI restriction endonuclease system. In particular, the present invention relates to DNA segments encoding the separate functional domains of this restriction endonuclease system.

The present invention also relates to the construction of two insertion mutants of FokI endonuclease.

Additionally, the present invention relates to a hybrid enzyme (Ubx-$F_N$) prepared by linking the Ultrabithorax Ubx homeo domain to the cleavage domain ($F_N$) of FokI.

2. Background Information

Type II endonucleases and modification methylases are bacterial enzymes that recognize specific sequences in duplex DNA. The endonuclease cleaves the DNA while the methylases methylate adenine or cytosine residues so as to protect the host-genome against cleavage [Type II restriction and modification enzymes. In Nucleases (Eds. Modrich and Roberts) Cold Spring Harbor Laboratory, New York, pp. 109–154, 1982]. These restriction-modification (R-M) systems function to protect cells from infection by phage and plasmid molecules that would otherwise destroy them.

As many as 2500 restriction enzymes with over 200 specificities have been detected and purified (Wilson and Murray, *Annu. Rev. Genet.* 25:585–627, 1991). The recognition sites of most of these enzymes are 4–6 base pairs long. The small size of the recognition sites is beneficial as the phage genomes are usually small and these small recognition sites occur more frequently in the phage.

Eighty different R-M systems belonging to the Type IIS class with over 35 specificities have been identified. This class is unique in that the cleavage site of the enzyme is separate from the recognition sequence. Usually the distance between the recognition site and the cleavage site is quite precise (Szybalski et al., *Gene*, 100:13–26, 1991). Among all these enzymes, the FokI restriction endonuclease is the most well characterized member of the Type IIS class. The FokI endonuclease (RFokI) recognizes asymmetric pentanucleotides in double-stranded DNA, 5' GGATG-3' (SEQ ID NO: 1) in one strand and 3'-CCTAC-5' (SEQ ID NO: 2) in the other, and introduces staggered cleavages at sites away from the recognition site (Sugisaki et al., *Gene* 16:73–78; 1981). In contrast, the FokI methylase (MFokI) modifies DNA thereby rendering the DNA resistant to digestion by FokI endonuclease. The FokI restriction and modification genes have been cloned and their nucleotide sequences deduced (Kita et al., *J. of Biol. Chem.*, 264:575–5756, 1989). Nevertheless, the domain structure of the FokI restriction endonuclease remains unknown, although a three domain structure has been suggested (Wilson and Murray, *Annu. Rev. Genet.* 25:585–627, 1991).

SUMMARY OF THE INVENTION

Accordingly, it is an object of the present invention to provide isolated domains of Type IIS restriction endonuclease.

It is another object of the present invention to provide hybrid restriction enzymes which are useful for mapping and sequencing of genomes.

An additional object of the present invention is to provide two insertion mutants of FOKI which have an increased distance of cleavage from the recognition site as compared to the wild-type enzyme. The polymerase chain reaction (PCR) is utilized to construct the two mutants.

Various other objects and advantages of the present invention will become obvious from the drawings and the following description of the invention.

In one embodiment, the present invention relates to a DNA segment encoding the recognition domain of a Type IIS endonuclease which contains the sequence-specific recognition activity of the Type IIS endonuclease or a DNA segment encoding the catalytic domain of a Type IIS endonuclease which contains the cleavage activity of the Type IIS endonuclease.

In another embodiment, the present invention relates to an isolated protein consisting essentially of the N-terminus or recognition domain of the FokI restriction endonuclease which protein has the sequence-specific recognition activity of the endonuclease or an isolated protein consisting essentially of the C-terminus or catalytic domain of the FokI restriction endonuclease which protein has the nuclease activity of the endonuclease.

In a further embodiment, the present invention relates to a DNA construct comprising a first DNA segment encoding the catalytic domain of a Type IIS endonuclease which contains the cleavage activity of the Type IIS endonuclease; a second DNA segment encoding a sequence-specific recognition domain other than the recognition domain of the Type IIS endonuclease; and a vector. In the construct, the first DNA segment and the second DNA segment are operably linked to the vector to result in the production of a hybrid restriction enzyme. The linkage occurs through a covalent bond.

Another embodiment of the present invention relates to a procaryotic cell comprising a first DNA segment encoding the catalytic domain of a Type IIS endonuclease which contains the cleavage activity of said Type IIS endonuclease; a second DNA segment encoding a sequence-specific recognition domain other than the recognition domain of said Type IIS endonuclease; and a vector. The first DNA segment and the second DNA are operably linked to the vector such that a single protein is produced. The first DNA segment may encode, for example, the catalytic domain ($F_N$) of FokI, and the second segment may encode, for example, the homeo domain of Ubx.

In another embodiment, the present invention relates to a hybrid restriction enzyme comprising the catalytic domain of a Type IIS endonuclease which contains the cleavage activity of the Type IIS endonuclease linked to a recognition domain of an enzyme or a protein other than the Type IIS endonuclease from which the cleavage domain is obtained.

In a further embodiment, the present invention relates to a DNA construct comprising a first DNA segment encoding the catalytic domain of a Type IIS endonuclease which contains the cleavage activity of the Type IIS endonuclease; a second DNA segment encoding a sequence-specific recognition domain other than the recognition domain of the Type IIS endonuclease; a third DNA segment comprising one or more codons, wherein the third DNA segment is inserted between the first DNA segment and the second DNA segment; and a vector. Preferably, the third segment contains four or seven codons.

In another embodiment, the present invention relates to a procaryotic cell comprising a first DNA segment encoding the catalytic domain of a Type IIS endonuclease which contains the cleavage activity of the Type IIS endonuclease; a second DNA segment encoding a sequence-specific recognition domain other than the recognition domain of the Type IIS endonuclease; a third DNA segment comprising one or more codons, wherein the third DNA segment is inserted between the first DNA segment and the second DNA segment; and a vector. The first DNA segment and the second DNA segment are operably linked to the vector so that a single protein is produced.

BRIEF DESCRIPTION OF THE DRAWINGS

FIG. 1 shows sequences of the 5' and 3' primers used to introduce new translation signals into fokIM and fokIR genes during PCR amplification. (SEQ ID NOs: 3-9). SD represents Shine-Dalgarno consensus RBS for Escherichia coli (E. coli) and 7-bp spacer separates the RBS from the ATG start condon. The fokIM primers are flanked by NcoI sites. The fokIR primers are flanked by BamHI sites. Start and stop codons are shown in bold letters. The 18-bp complement sequence is complementary to the sequence immediately following the stop codon of MfokI gene.

(A) The cleavage properties of the tryptic fragments were analyzed by agarose gel electrophoresis. 1 μg of pTZ19R in 10 mM Tris.HCl (pH 8), 50 mM NaCl, 1 mM DTT, and 10 mM $MgCl_2$ was digested with 2 μl of the solution containing the fragments (tryptic digests, breakthrough and eluate respectively) at 37° C. for 1 hr in a reaction volume of 10 μl. Lanes 4 to 6 correspond to trypsin digestion of Fok I- oligo complex in absence of $MgCl_2$. Lanes 7 to 9 correspond to trypsin digestion of FokI - oligo complex in presence of 10 mM $MgCl_2$. Lanes: 1, 1 kb ladder; 2, pTZ19R; 3, pTZ19R digested with FokI endonuclease; 4 and 6, reaction mixture of the tryptic digests of FokI - oligo complex; 5 and 7, 25 kDa C-terminal fragment in the breakthrough volume; 6 and 9, tryptic fragments of FokI that bound to the DEAE column. The intense bands at bottom of the gel correspond to excess oligonucleotides.

(B) SDS (0.1%)—polyacrylamide (12%) gel electrophoretic profiles of fragments from the DEAE column. Lanes 3 to 5 correspond to trypsin digestion of FokI - oligo complex in absence of $MgCl_2$. Lanes 6 to 8 correspond to trypsin digestion of FokI - oligo complex in presence of 10 mM $MgCl_2$. Lanes: 1, protein standards; 2, FokI endonuclease; 3 and 6, reaction mixture of the tryptic digests of FokI - oligo complex; 4 and 7, 25 kDa C-terminal fragment in the breakthrough volume; 5 and 8, tryptic fragments of FokI that bound to the DEAE column.

Figures 7A, 7B:

FIG. 7 shows an analysis of sequence—specific binding of DNA by 41 kDa N-terminal fragment using gel mobility shift assays. For the exchange reaction, the complex (10 μl) was incubated with 1 μl of 32P-labeled specific (or non-specific) oligonucleotide duplex in a volume of 20 μl containing 10 mM Tris.HCl, 50 mM NaCl and 10 mM $MgCl_2$ at 37° C. for various times. 1 μl of the 5'-$^{32}$P-labeled specific probe [d-5'-CCTCTGGATGCTCTC-3'(SEQ ID NO: 10): 5'-GAGAGCATCCAGAGG-3' (SEQ ID NO: 11)] contained 12 picomoles of the duplex and $\sim 50 \times 10^3$ cpm. 1 μl of the 5'-$^{32}$P-labeled non-specific probe [5'-TAATTGATTCTTAA-3'(SEQ ID NO: 12):5'-ATTAAGAATCAATT-3' (SEQ ID NO: 13)] contained 12 picomoles of the duplex and $\sim 25 \times 10^3$ cpm. (A) Lanes: 1, specific oligonucleotide duplex; 2, 41 kDa N-terminal fragment-oligo complex; 3 and 4, specific probe incubated with the complex for 30 and 120 min respectively. (B) Lanes: 1, non-specific oligonucleotide duplex; 2, 41 kDa N-terminal fragment-oligo complex; 3 and 4 non-specific probe incubated with the complex for 30 and 120 min respectively.

FIG. 8 shows SDS (0.1%) polyacrylamide (12%) gel electrophoretic profiles of tryptic fragments at various time points of trypsin digestion of FokI endonuclease. The enzyme (200 μg) in a final volume of 200 μl containing 10 mM Tris.HCl, 50 mM NaCl and 10 mM $MgCl_2$ was digested with trypsin at RT. The trypsin to FokI ratio was 1:50 by weight. Aliquots (28 μl) from the reaction mixture removed at different time intervals and quenched with excess antipain. Lanes: 1, protein standards; 2, FokI endonuclease; 3, 2.5 min; 4, 5.0 min; 5, 10 min; 6, 20 min; 7, 40 min; 8, 80 min; and 9, 160 min of trypsin digestion respectively.

Figure 9:
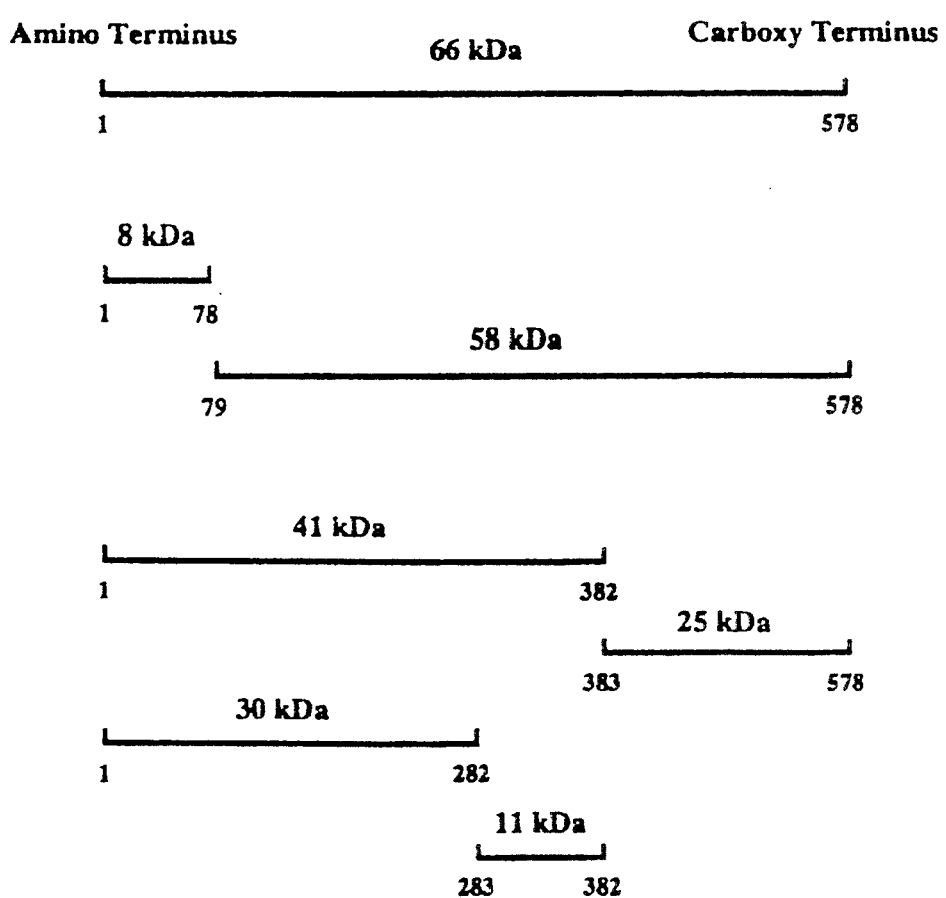

FIG. 9 shows the tryptic map of FokI endonuclease (A) FokI endonuclease fragmentation pattern in absence of the oligonucleotide substrate. (B) FokI endonuclease fragmentation pattern in presence of the oligonucleotide substrate.

FIG. 10 shows the predicted secondary structure of FokI based on its primary sequencing using the PREDICT program (see SEQ ID NO:31). The trypsin cleavage site of FokI in the presence of DNA substrates is indicated by the arrow. The KSELEEKKSEL segment is highlighted. The symbols are as follows: h, helix; s, sheet; and , random coil.

FIG. 11 shows the sequences of the 5' and 3' oligonucleotide primers used to construct the insertion mutants of FokI (see SEQ ID NO:32, SEQ ID NO:33, SEQ ID NO:34, SEQ ID NO:35, SEQ ID NO:36, SEQ ID NO:37, SEQ ID NO:38 and SEQ ID N0:39, respectively). The four and seven codon inserts are shown in bold letters. The amino acid sequence is indicated over the nucleotide sequence. The same 3' primer was used in the PCR amplification of both insertion mutants.

Figure 12:
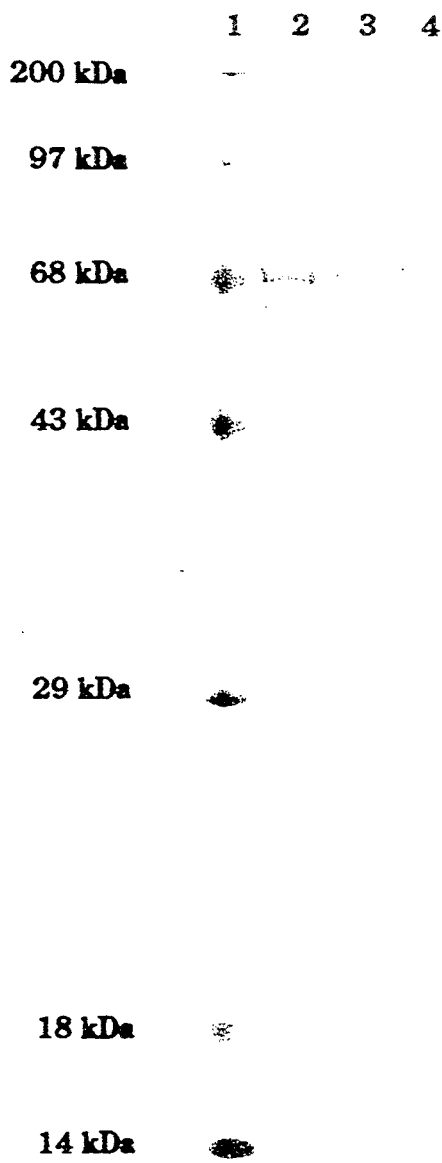

FIG. 12 shows the SDS/PAGE profiles of the mutant enzymes purified to homogeneity. Lanes: 1, protein standards; 2, FokI; 3, mutant FokI with 4-codon insertion; and 4, mutant FokI with 7-codon insertion.

FIG. 13 shows an analysis of the DNA sequence specificity of the mutant enzymes. The DNA substrates were digested in 10 mM Tris HCl, pH 8.0/50 mM NaCl/1 mM DTT/10 mM $MgCl_2$ at 37° C. for 2 hrs.

(A) Cleavage pattern of pTZ19R DNA substrate analyzed by 1% agarose gel electrophoresis. 2 μg of pTZ19R DNA was used in each reaction. Lanes: 1, 1-kilobase (kb) ladder; 2, pTZ19R; 3, pTZ19R digested with FokI; pTZ19R digested with mutant FokI with 4-codon insertion; and 5, pTZ19R digested with mutant FokI with 7-codon insertion.

(B) Cleavage pattern of 256 bp DNA substrate containing a single FokI site analyzed by 1.5% agarose gel electrophoresis. 1 μg of radiolabeled substrates ($^{32}P$-labeled on individual strands) was digested as described above. The agarose gel was stained with ethidium bromide and visualized under UV light. Lanes 2 to 6 correspond to the $^{32}P$-labeled substrate in which the 5'-CATCC-3' strand is $^{32}$-P labeled. Lanes 7 to 11 correspond to the substrate in which the 5'-GGATG-3' strand is $^{32}P$-labeled. Lanes: 1, 1 kb ladder; 2 and 7, $^{32}P$-labeled 250 bp DNA substrates; 3 and 8, $^{32}$-P labeled substrates cleaved with FokI; 4 and 9, purified the laboratory wild-type FokI; 5 and 10, mutant FokI with 4-codon insertion; 6 and 11, mutant FokI with 7-codon insertion.

(C) Autoradiograph of the agarose gel from above. Lanes: 2 to 11, same as in B.

FIG. 14 shows an analysis of the distance of cleavage from the recognition site by FokI and the mutant enzymes. The unphosphorylated oligonucleotides were used for dideoxy DNA sequencing with pTZ19R as the template. The sequencing products (G, A, T, C) were electrophoresed on a 6% acrylamide gel containing 7M urea, and the gel dried. The products were then exposed to an x-ray film for 2 hrs. Cleavage products from the 100 bp and the 256 bp DNA substrates are shown in A and B, respectively. I corresponds to substrates containing $^{32}P$-label on the 5'-GGATG-3' strand, and II corresponds to substrates containing 32P-label on the 5'-CATCC-3' strand. Lanes: 1, FokI; 2, FokI; 3, mutant FokI with 4-codon insertion; and 4, mutant FokI with 7-codon insertion.

Figure 15B:
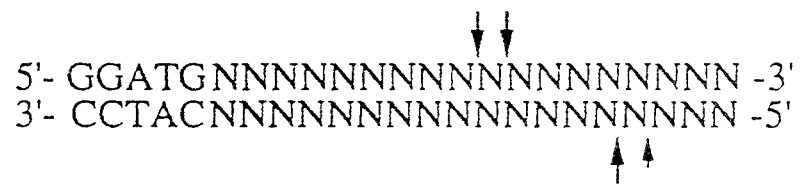
Figure 15C:

FIG. 15 shows a map of the cleavage site(s) of FokI and the mutant enzymes based on the 100 bp DNA substrate containing a single FokI site: (A) wild-type FokI; (B) mutant FokI with 4-codon insertion; and (C) mutant FokI with 7-codon insertion (see SEQ ID NO:40). The sites of cleavage are indicated by the arrows. Major cleavage sites are shown by larger arrows.

Figure 16:
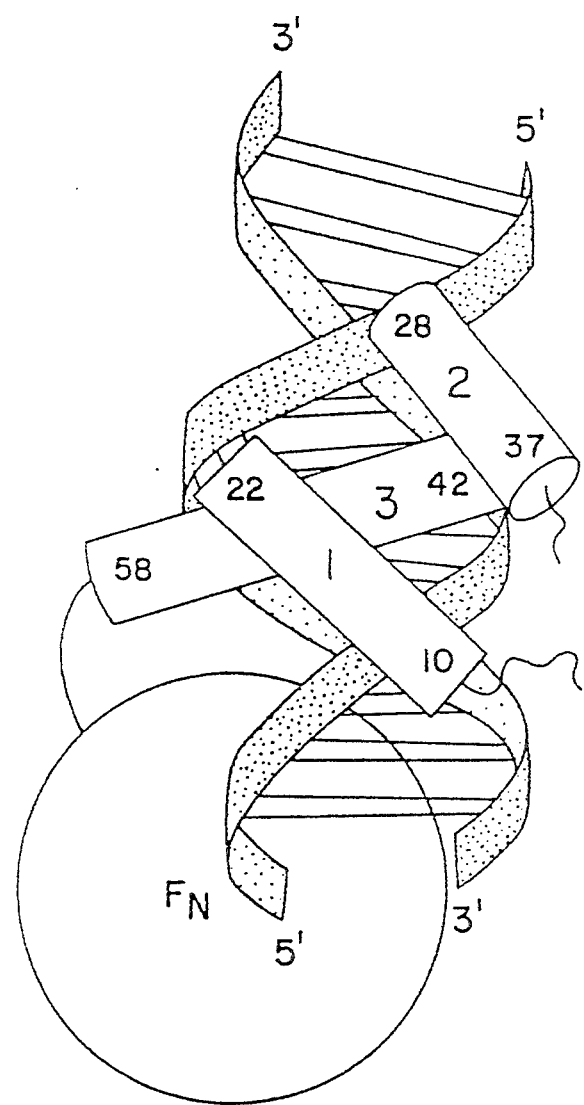

FIG. 16 represents a diagram showing the orientation of the Ubx homeo domain with respect to the FokI nuclease domain ($F_N$) in relation to the DNA substrate. The crystal structure of an engrailed homeo domain—DNA complex was reported by Kissinger et al. (*Cell* 63:579–90 (1990)). The large numbers 1, 2 and 3 indicate α-helices and the smaller numbers at either end of these helices indicate amino acid residue positions.

FIG. 17 shows the construction of expression vectors of the Ubx-$F_N$ hybrid enzyme. (A) Sequences of the 5' and 3' primers used to construct the hybrid gene, Ubx-$F_N$. The Ubx primers are flanked by PstI and SpeI sites (see SEQ ID NO:41 and SEQ ID NO:42). The Ubx-$F_N$ primers are flanked by NdeI and BamHI sites (see SEQ ID NO:43 and SEQ ID NO:44). Start and stop codons are shown in boldface letters. (B) Structure of plasmids, pRRS Ubx-$F_N$ and pET-15b Ubx-$F_N$. The PCR modified Ubx homeo box was substituted for the PstI/SpeI fragment of pRRSfokIR to generate pRRS Ubx-$F_N$. The PCR-generated fragment using Ubx-$F_N$ primers was inserted at the BamHI/NdeI sites of pET-15b to form pET-15b Ubx-$F_N$.

FIG. 18 represents SDS/PAGE profiles at each step in the purification of the Ubx-$F_N$ hybrid enzyme. Lanes: 1, protein standards; 2, crude extract from induced cells; 3, His-bind resin pool; 4, phosphocellulose pool; and 5, DEAE pool.

Figure 19A:
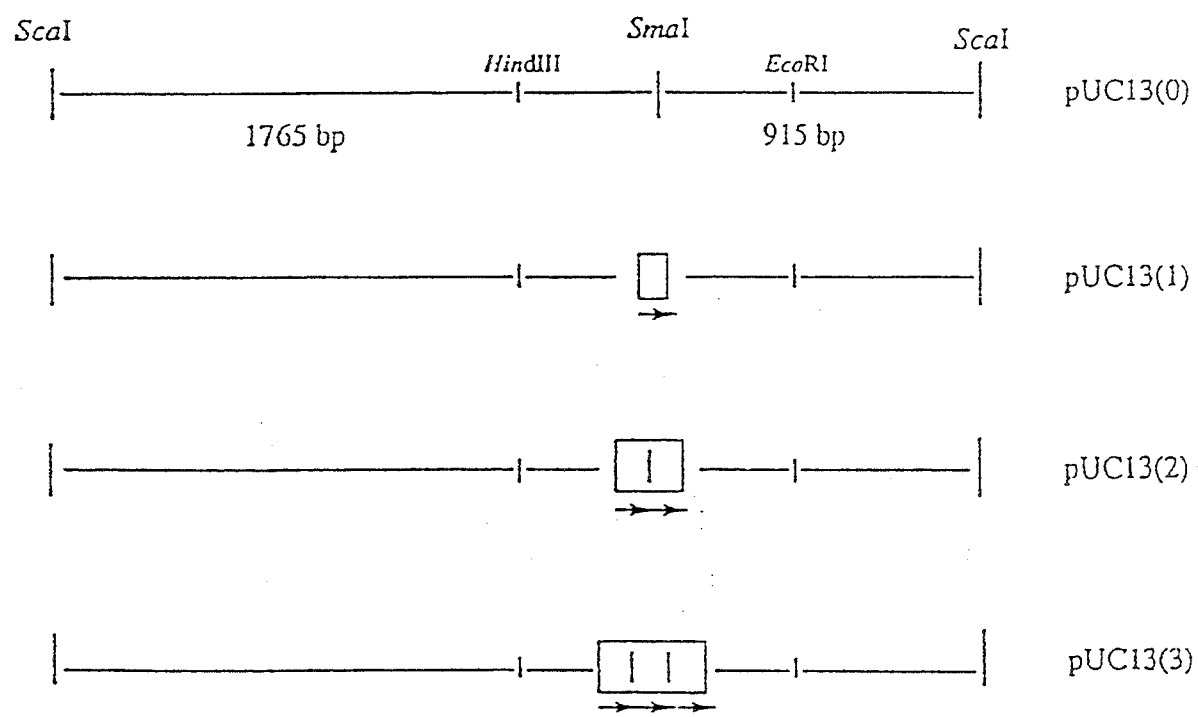

FIG. 19 shows a characterization of the Ubx-$F_N$ hybrid protein using the linearized pUC13 DNA substrates containing Ubx site(s). (A) pUC13 derived DNA substrates. □:30 bp insert containing the Ubx site, 5'-TTAATGGTT-3'. The number of tandem repeats of the 30 bp insert in these substrates are shown in brackets. The orientation of the Ubx site(s) are indicated by the arrows. (B) The DNA substrate (1 μg) was partially digested in buffer containing 20 mM Tris. HCl (pH 7.6), 75 mM KCl, 1 mM DTT, 50 μg/ml BSA, 10% glycerol, 100 mg/ml tRNA and 2 mM $MgCl_2$ at 31° C. for 4–5 hrs. The products were analyzed by 1% agarose gel electrophoresis. The substrate was present in large excess compared to the Ubx-$F_N$ hybrid protein (~100:1). The reaction condition was optimized to yield a single double-stranded cleavage per substrate molecule. The reaction proceeds to completion upon increasing the enzyme concentration or by digesting overnight at 31° C. (data not shown). The two fragments, ~1.8 kb and ~0.95 kb, respectively, resulting from the binding of the hybrid enzyme at the newly inserted Ubx site of pUC13 and cleaving near this site, are indicated by the arrows. Lane 1 contains molecular weight makers. Lane 2 corresponds to undigested pUC13 without any insert. Lane 3 corresponds to pUC13 without any insert digested with Ubx-$F_n$. Lanes 4–6 correspond to pUC13 having 1, 2 or 3 inserts, respectively, digested with Ubx-$F_n$.

Figure 20B:
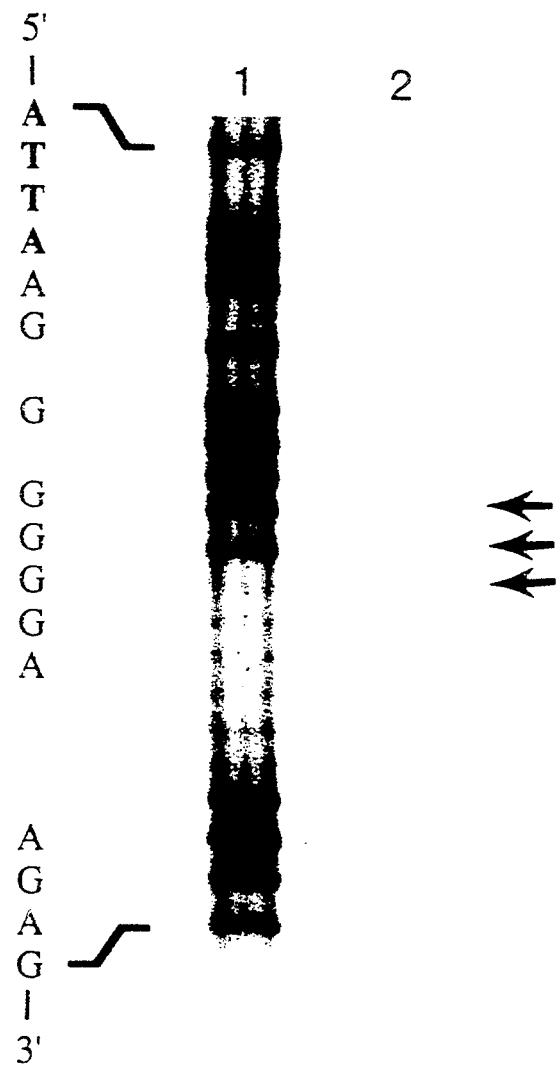

FIG. 20 shows an analysis of the distance of cleavage from the recognition site by Ubx-F$_N$. The cleavage products of the $^{32}$P-labeled DNA substrate containing a single Ubx site by Ubx-F$_N$ along with (G+A) Maxam-Gilbert sequencing reactions were separated by electrophoresis on a 6% polyacrylamide gel containing 6M urea, and the gel was dried and exposed to an x-ray film for 6 hrs. (A) corresponds to cleavage product(s) from a substrate containing $^{32}$P-label on the 5'-TAAT-3' strand (see SEQ ID NO:45). Lanes: 1, (G+A) sequencing reaction; and 2, Ubx-F$_N$. (B) corresponds to a substrate containing $^{32}$P-label on the complementary strand, 5'-ATTA-3'(SEQ ID NO:46). Lanes: 1, (G+A) sequencing reaction; 2, Ubx-F$_N$. (C) A map of the cleavage site(s) of Ubx-F$_N$ based on the DNA substrate containing a single Ubx site. The recognition site is shown by outline letters. The site(s) of cleavage are indicated by the arrows. The purine residues are indicated by * (see SEQ ID NO:47 and SEQ ID NO:48).

DETAILED DESCRIPTION OF THE INVENTION

The present invention is based on the identification and characterization of the functional domains of the FokI restriction endonuclease. In the experiments resulting in the present invention, it was discovered that the FokI restriction endonuclease is a two domain system, one domain of which possesses the sequence-specific recognition activity while the other domain contains the nuclease cleavage activity.

The FokI restriction endonuclease recognizes the non-palindromic pentanucleotide 5'-GGATG-3'(SEQ ID NO:1):5'-CATCC-3'(SEQ ID NO:2) in duplex DNA and cleaves 9/13 nucleotides downstream from the recognition site. Since 10 base pairs are required for one turn of the DNA helix, the present inventor hypothesized that the enzyme would interact with one face of the DNA by binding at one point and cleave at another point on the next turn of the helix. This suggested the presence of two separate protein domains, one for sequence-specific recognition of DNA and one for endonuclease activity. The hypothesized two domain structure was shown to be the correct structure of the FokI endonuclease system by studies that resulted in the present invention.

Accordingly, in one embodiment, the present invention relates to a DNA segment which encodes the N-terminus of the FokI restriction endonuclease (preferably, about the N-terminal ⅔'s of the protein). This DNA segment encodes a protein which has the sequence-specific recognition activity of the endonuclease, that is, the encoded protein recognizes the non-palindromic pentanucleotide d-5'-GGATG-3'(SEQ ID NO:1):5'-CATCC-3'(SEQ ID NO:2) in duplex DNA. Preferably, the DNA segment of the present invention encodes amino acids 1-382 of the FokI endonuclease.

In a further embodiment, the present invention relates to a DNA segment which encodes the C-terminus of the FokI restriction endonuclease. The protein encoded by this DNA segment of the present invention has the nuclease cleavage activity of the FokI restriction endonuclease. Preferably, the DNA segment of the present invention encodes amino acids 383-578 of the FokI endonuclease. DNA segments of the present invention can be readily isolated from biological samples using methods known in the art, for example, gel electrophoresis, affinity chromatography, polymerase chain reaction (PCR), or a combination thereof. Further, the DNA segments of the present invention can be chemically synthesized using standard methods in the art.

The present invention also relates to the proteins encoded by the DNA segments of the present invention. Thus, in another embodiment, the present invention relates to a protein consisting essentially of the N-terminus of the FokI endonuclease which retains the sequence-specific recognition activity of the enzyme. This protein of the present invention has a molecular weight of about 41 kilodaltons as determined by SDS polyacrylamide gel electrophoresis in the presence of 2-mercaptoethanol.

In a further embodiment, the present invention relates to a protein consisting essentially of the C-terminus of the FokI restriction endonuclease (preferably, the C-terminal ⅓ of the protein). The molecular weight of this protein is about 25 kilodaltons as determined by SDS/polyacrylamide gel electrophoresis in the presence of 2-mercaptoethanol.

The proteins of the present invention can be isolated or purified from a biological sample using methods known in the art. For example, the proteins can be obtained by isolating and cleaving the FokI restriction endonuclease. Alternatively, the proteins of the present invention can be chemically synthesized or produced using recombinant DNA technology and purified.

The DNA segments of the present invention can be used to generate 'hybrid' restriction enzymes by linking other DNA binding protein domains with the nuclease or cleavage domain of FokI. This can be achieved chemically as well as by recombinant DNA technology. Such chimeric hybrid enzymes have novel sequence specificity and are useful for physical mapping and sequencing of genomes of various species, such as, humans, mice and plants. For example, such enzymes would be suitable for use in mapping the human genome. These engineered hybrid endonucleases will also facilitate the manipulation of genomic DNA and provide valuable information about protein structure and protein design.

Such chimeric enzymes are also valuable research tools in recombinant DNA technology and molecular biology. Currently only 4-6 base pair cutters and a few 8 base pair cutters are available commercially. (There are about 10 endonucleases which cut >6 base pairs that are available commercially.) By linking other DNA binding proteins to the nuclease domain of FokI new enzymes can be generated that recognize more than 6 base pairs in DNA.

Accordingly, in a further embodiment, the present invention relates to a DNA construct and the hybrid restriction enzyme encoded therein. The DNA construct of the present invention comprises a first DNA segment encoding the nuclease domain of the FokI restriction endonuclease, a second DNA segment encoding a sequence-specific recognition domain and a vector. The first DNA segment and the second DNA segment are operably linked to the vector so that expression of the segments can be effected thereby yielding a chimeric restriction enzyme. The construct can comprise regulatory elements such as promoters (for example, T7, tac, trp and lac UV5 promoters), transcriptional terminators or retroregulators (for example, stem loops). Host cells (procaryotes such as E. coli) can be transformed with the DNA constructs of the present invention and used for the production of chimeric restriction enzymes.

The hybrid enzymes of the present invention are comprised of the nuclease domain of FokI linked to a recognition domain of another enzyme or DNA binding protein (such as, naturally occurring DNA binding proteins that recognize 6 base pairs). Suitable recognition domains include, but are not limited to, the recognition domains of zinc finger motifs; homeo domain motifs; POU domains (eukaryotic transcription regulators, e.g., Pit1, Oct1, Oct2 and unc86); other DNA binding protein domains of lambda repressor, lac repressor, cro, gal4; DNA binding protein domains of oncogenes such as myc, jun; and other naturally occurring sequence-specific DNA binding proteins that recognize >6 base pairs.

The hybrid restriction enzymes of the present invention can be produced by those skilled in the art using known methodology. For example, the enzymes can be chemically synthesized or produced using recombinant DNA technology well known in the art. The hybrid enzymes of the present invention can be produced by culturing host cells (such as, HB101, RR1, RB791 and MM294) containing the DNA construct of the present invention and isolating the protein. Further, the hybrid enzymes can be chemically synthesized, for example, by linking the nuclease domain of the FokI to the recognition domain using common linkage methods known in the art, for example, using protein cross-linking agents such as EDC/NHS, DSP, etc.

One particular hybrid enzyme which can be created according to the present invention and, thus, an embodiment of the present invention is Ubx-$F_N$. The chimeric restriction endonuclease can be produced by linking the Ubx homeo domain to the cleavage domain ($F_N$) of FokI. Subsequent to purification, the properties of the hybrid enzyme were analyzed.

While the FokI restriction endonuclease was the enzyme studied in the following experiments, it is expected that other Type IIS endonucleases (such as, those listed in Table 2) will function using a similar two domain structure which one skilled in the art could readily determine based on the present invention.

Recently, StsI, a heteroschizomer of FokI has been isolated from Streptococcus sanguis (Kita et al., Nucleic Acids Research 20 (3)) 618, 1992). StsI recognizes the same nonpalindromic pentadeoxyribonucleotide 5'-GGATG-3':5'-CATCC-3' as FokI but cleaves 10/14 nucleotides downstream of the recognition site. The StsI RM system has been cloned and sequenced (Kita et al., Nucleic Acids Research 20 (16) 4167-72, 1992). Considerable amino acid sequence homology (~30%) has been detected between the endonucleases, FokI and StsI.

Another embodiment of the invention relates to the construction of two insertion mutants of FokI endonuclease using the polymerase chain reaction (PCR). In particular, this embodiment includes a DNA construct comprising a first DNA segment encoding the catalytic domain of a Type IIS endonuclease which contains the cleavage activity of the Type IIS endonuclease, a second DNA segment encoding a sequence-specific recognition domain other than the recognition domain of the Type IIS endonuclease, and a third DNA segment comprising one or more codons. The third DNA segment is inserted between the first DNA segment and the second DNA segment. The construct also includes a vector. The Type IIS endonuclease is FokI restriction endonuclease.

Suitable recognition domains include, but are not limited to, zinc finger motifs, homeo domain motifs, POU domains, DNA binding domains of repressors, DNA binding domains of oncogenes and naturally occurring sequence-specific DNA binding proteins that recognize >6 base pairs.

As noted above, the recognition domain of FokI restriction endonuclease is at the amino terminus of FokI endonuclease, whereas the cleavage domain is probably at the carboxyl terminal third of the molecule. It is likely that the domains are connected by a linker region, which defines the spacing between the recognition and the cleavage sites of the DNA substrate. This linker region of FokI is susceptible to cleavage by trypsin in the presence of a DNA substrate yielding a 41-kDa amino-terminal fragment (The DNA binding domain) and a 25 kDa carboxyl-terminal fragment (the cleavage domain). Secondary structure prediction of FokI endonuclease based on its primary amino acid sequence supports this hypothesis (see FIG. 10). The predicted structure reveals a long stretch of alpha helix region at the junction of the recognition and cleavage domains. This helix probably constitutes the linker which connects the two domains of the enzyme. Thus, it was thought that the cleavage distance of FokI from the recognition site could be altered by changing the length of this spacer (the alpha helix). Since 3.6 amino acids are required to form one turn of the alpha helix, insertion of either four codons or seven codons in this region would extend the pre-existing helix in the native enzyme by one or two turns, respectively. Close examination of the amino acid sequence of this helix region revealed the presence of two KSEL repeats separated by amino acids EEK (FIG. 10) (see SEQ ID NO:21). The segments KSEL (4 codons) (see SEQ ID NO:22) and KSELEEK (7 codons) (see SEQ ID NO:23) appeared to be good choices for insertion within this helix in order to extend it by one and two turns, respectively. (See Examples X and XI.) Thus, genetic engineering was utilized in order to create mutant enzymes.

In particular, the mutants are obtained by inserting one or more, and preferably four or seven, codons between the recognition and cleavage domains of FokI. More specifically, the four or seven codons are inserted at nucleotide 1152 of the gene encoding the endonuclease. The mutants have the same DNA sequence specificity as the wild-type enzyme. However, they cleave one nucleotide further away from the recognition site on both strands of the DNA substrates as compared to the wild-type enzyme.

Analysis of the cut sites of FokI and the mutants, based on the cleavage of the 100 bp fragment, is summarized in FIG. 15. Insertion of four (or seven) codons between the recognition and cleavage domains of FokI is accompanied by an increase in the distance of cleavage from the recognition site. This information further supports the presence of two separate protein domains within the FokI endonuclease: one for the sequence specific recognition and the other for the endonuclease activity. The two domains are connected by a linker region which defines the spacing between the recognition and the cleavage sites of the DNA substrate. The modular structure of the enzyme suggests it may be feasible to construct chimeric endonucleases of different sequence specificity by linking other DNA-binding proteins to the cleavage domain of the FokI endonuclease.

In view of the above-information, another embodiment of the invention includes a procaryotic cell comprising a first DNA segment encoding the catalytic domain of a Type IIS endonuclease which contains the cleavage activity of the Type IIS endonuclease, a second DNA segment encoding a sequence-specific recognition domain other than the recognition domain of the Type IIS endonuclease, and a third DNA segment comprising one or more codons. The third DNA segment is inserted between the first DNA segment and the second DNA segment. The cell also includes a vector. Additionally, it should be noted that the first DNA segment, the second DNA segment, and the third DNA segment are operably linked to the vector so that a single protein is produced. The third segment may consist essentially of four or seven codons.

The present invention also includes the protein produced by the procaryotic cell referred to directly above. In particular, the isolated protein consists essentially of the recognition domain of the FokI restriction endonuclease, the catalytic domain of the FokI restriction endonuclease, and amino acids encoded by the codons present in the third DNA segment.

The following non-limiting Examples are provided to describe the present invention in greater detail.

EXAMPLES

The following materials and methods were utilized in the isolation and characterization of the FokI restriction endonuclease functional domains as exemplified hereinbelow.

Bacterial Strains and Plasmids

Recombinant plasmids were transformed into $E. coli$ RB791 i$^q$ cells which carry the lac i$^q$ allele on the chromosome (Brent and Ptashne, PNAS USA, 78:4204–4208, 1981) or $E. coli$ RR1 cells. Plasmid pACYCfokIM is a derivative of pACYC184 carrying the PCR-generated fokIM gene inserted into NcoI site. The plasmid expresses the FokI methylase constitutively and was present in RB791 cells (or RR1 cells) whenever the fokIR gene was introduced on a separate compatible plasmid. The FokI methylase modifies FokI sites and provides protection against chromosomal cleavage. The construction of vectors pRRS and pCB are described elsewhere (Skoglund et al., Gene, 88:1–5, 1990).

Enzymes, Biochemicals and Oligos

Oligo primers for PCR were synthesized with an Applied Biosystem DNA synthesizer using cyanoethyl phosphoramidite chemistry and purified by reversed phase HPLC. Restriction enzymes were purchased from New England Biolabs. The DNA ligase IPTG were from Boehringer-Mannheim. PCR reagents were purchased as a Gene Amp Kit from Perkin-Elmer. Plasmid purification kit was from QIAGEN.

Restriction Enzyme Assays

Cells from a 5-ml sample of culture medium were harvested by centrifugation, resuspended in 0.5 ml sonication buffer [50 mM Tris.HCl (pH 8), 14 mM 2-mercaptoethanol], and disrupted by sonication (3×5 seconds each) on ice. The cellular debris was centrifuged and the crude extract used in the enzyme assay. Reaction mixtures (10 μl) contained 10 mM Tris. HCl (pH 8), 10 mM MgCl$_2$, 7 mM 2-mercaptoethanol, 50 μg of BSA, 1 μg of plasmid pTZ19R (U.S. biochemicals) and 1 μl of crude enzyme. Incubation was at 37° C. for 15 min. tRNA (10 μg) was added to the reaction mixtures when necessary to inhibit non-specific nucleases. After digestion, 1 μl of dye solution (100 mM EDTA, 0.1% bromophenol blue, 0.1% xylene cyanol, 50% glycerol) was added, and the samples were electrophoresed on a 1% agarose gel. Bands were stained with 0.5 μg ethidium bromide/ml and visualized with 310-nm ultraviolet light.

SDS/PAGE

Proteins were prepared in sample buffer and electrophoresed in SDS (0.1%)—polyacrylamide (12%) gels as described by Laemmli (Laemmli, Nature, 222:680–685, 1970). Proteins were stained with coomassie blue.

EXAMPLE I

Cloning of FokI RM System

The FokI system was cloned by selecting for the modification phenotype. $Flavobacterium$ $okeanokoites$ strain DNA was isolated by the method described by Caserta et al. (Caserta et al., J. Biol. Chem., 262:4770–4777, 1987). Several $Flavobacterium$ $okeanokoites$ genome libraries were constructed in plasmids pBR322 and pUC13 using the cloning enzymes PstI, BamHI and BglII. Plasmid library DNA (10 μg) was digested with 100 units of FokI endonuclease to select for plasmids expressing fokIM+ phenotype.

Surviving plasmids were transformed into RR1 cells and transformants were selected on plates containing appropriate antibiotic. After two rounds of biochemical enrichment, several plasmids expressing the fokIM+ phenotype from these libraries were identified. Plasmids from these clones were totally resistant to digestion by FokI.

Among eight transformants that were analyzed from the $F.$ $okeanokoites$ pBR322 PstI library, two appeared to carry the fokIM gene and plasmids from these contained a 5.5 kb PstI fragment. Among eight transformants that were picked from $F.$ $okeanokoites$ pBR322 BamHI library, two appeared to carry the fokIM gene and their plasmids contained ~18 kb BamHI fragment. Among eight transformants that were analyzed from the $F.$ $okeanokoites$ genome BglII library in pUC13, six appeared to carry the fokIM gene. Three of these clones had a 8 kb BglII insert while the rest contained a 16 kb BglII fragment.

Plating efficiency of phage λ on these clones suggested that they also carried the fokIR gene. The clones with the 8-kb BglII insert appeared to be most resistant to phage infection. Furthermore, the FokI endonuclease activity was detected in the crude extract of this clone after partial purification on a phosphocellulose column. The plasmid, pUCfokIRM from this clone was chosen for further characterization.

The 5.5 kb PstI fragment was transferred to M13 phages and the nucleotide sequences of parts of this insert determined using Sanger's sequencing method (Sanger et al., PNAS USA, 74:5463–5467, 1977). The complete nucleotide sequence of the FokI RM system has been published by other laboratories (Looney et al., Gene, 80:193–208, 1989; Kita et al., Nucleic Acid Res., 17:8741–8753, 1989; Kita et al., J. Biol. Chem. 264:5751–5756, 1989).

EXAMPLE II

Construction of an Efficient Overproducer Clone of FokI Endonuclease using Polymerase Chain Reaction The PCR technique was used to alter transcriptional and translational signals surrounding the fokIR gene so as to achieve overexpression in E.coli (Skoglund et al., Gene, 88:1-5, 1990). The ribosome-binding site preceding the fokIR and fokIM genes were altered to match the consensus E. coli signal.

In the PCR reaction, plasmid pUCfokIRM DNA linearized with BamHI was used as the template. PCR reactions (100 μl) contained 0.25 nmol of each primer, 50 μM of each dNTP, 10 mM Tris.HCl (pH 8.3 at 25° C.), 50 mM KCl, 1.5 mM MgCl$_2$ 0.01% (W/V) gelatin, 1 ng of template DNA, 5 units of Taq DNA polymerase. The oligo primes used for the amplification of the fokIR and fokIM genes are shown in FIG. 1. Reaction mixtures (ran in quadruplicate) were overlayed with mineral oil and reactions were carried out using Perkin-Elmer-Cetus Thermal Cycler.

Initial template denaturation was programmed for 2 min. Thereafter, the cycle profile was programmed as follows: 2 min at 37° C. (annealing), 5 min at 72° C. (extension), and 1 min at 94° C. (denaturation). This profile was repeated for 25 cycles and the final 72° C. extension was increased to 10 min. The aqueous layers of the reaction mixtures were pooled and extracted once with 1:1 phenol/chloroform and twice with chloroform. The DNA was ethanol-precipitated and resuspended in 20 μl TE buffer [10 mM Tris.HCl, (pH 7.5), 1 mM EDTA]. The DNA was then cleaved with appropriate restriction enzymes to generate cohesive ends and gel-purified.

The construction of an over-producer clone was done in two steps. First, the PCR-generated DNA containing the fokIM gene was digested with NcoI and gel purified. It was then ligated into NcoI-cleaved and dephosphorylated pACYC184 and the recombinant DNA transfected into E.coli RB791 i$^q$ or RR1 cells made competent as described by Maniatis et al (Maniatis et al., Molecular Cloning. A laboratory manual Cold Spring Harbor Laboratory, Cold Spring Harbor, NY, 1982). After Tc selection, several clones were picked and plasmid DNA was examined by restriction analysis for the presence of fokIM gene fragment in correct orientation to the chloramphenicol promoter of the vector (see FIG. 2). This plasmid expresses FokI methylase constitutively, and this protects the host from chromosomal cleavage when the fokIR gene is introduced into the host on a compatible plasmid. The plasmid DNA from these clones are therefore resistant to FokI digestion.

Second, the PCR-generated fokIR fragment was ligated into BamHI-cleaved and dephosphorylated high expression vectors pRRS or pCB. pRRS possesses a lac UV5 promoter and pCB containing the strong tac promoter. In addition, these vectors contain the positive retroregulator stem-loop sequence derived from the crystal protein-encoding gene of Bacillus Thuringiensis downstream of the inserted fokIR gene. The recombinant DNA was transfected into competent E.coli RB791 i$^q$ [pACYCfokIM] or RR1[pACYCfokIM]cells. After Tc and Ap antibiotic selection, several clones were picked and plasmid DNA was examined by restriction analysis for fokIR gene fragment in correct orientation for expression from the vector promoters. These constructs were then examined for enzyme production.

Figure 2A:
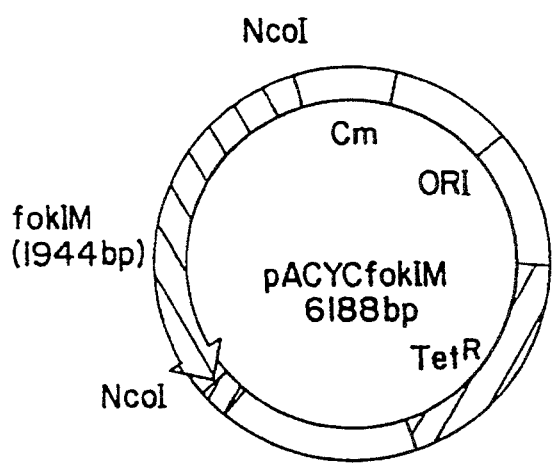
FIG. 2 shows the structure of plasmids pACYCMfokIM, pRRSRfokIR and pCBfokIR. The PCR-modified fokIM gene was inserted at the NcoI site of pACYC184 to form pACYCfokIM. The PCR-generated fokIR gene was inserted at the BamHI sites of pRRS and pCB to form pRRSfokIR and pCBfokIR, respectively. pRRS possesses a lac UV5 promoter and pCB contains a strong tac promoter. In addition, these vectors contain the positive retroregulator sequence downstream of the inserted fokIR gene.
Figure 2B:
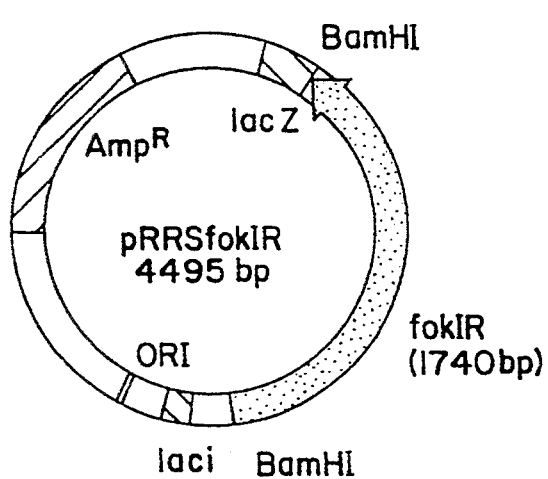
Figure 2C:
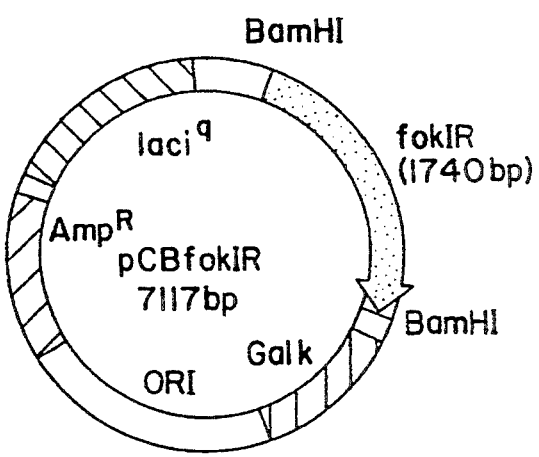

To produce the enzyme, plasmid-containing RB791 i$^q$ or RR1 cells were grown at 37° C. with shaking in 2× concentrated TY medium [1.6% tryptone, 1% yeast extract, 0.5% NaCl (pH 7.2)] supplemented with 20 μg Tc/ml (except for the pUCfokIRM plasmid) and 50 μg Ap/ml. IPTG was added to a concentration of 1 mM when the cell density reached O.D.$_{600}$=0.8. The cells were incubated overnight (12 hr) with shaking. As is shown in FIG. 2, both constructs yield FokI to a level of 5-8% of the total cellular protein.

EXAMPLE III

Purification of FoKI Endonuclease

A simple three-step purification procedure was used to obtain electrophoretically homogeneous FokI endonuclease. RR1 [pACYCfokIM, pRRSfokIR] were grown in 6 L of 2×TY containing 20 μg Tc/ml and 50 μg/Ap ml at 37° C. to A$_{600}$=0.8. and then induced overnight with 1 mM IPTG. The cells were harvested by centrifugation and then resuspended in 250 ml of buffer A [10 mM Tris.phosphate (pH 8.0), 7 mM 2-mercaptoethanol, 1 mM EDTA, 10% glycerol] containing 50 mM NaCl.

The cells were disrupted at maximum intensity on a Branson Sonicator for 1 hr at 4° C. The sonicated cells were centrifuged at 12,000 g for 2 hr at 4° C. The supernatant was then diluted to 1 L with buffer A containing 50 mM NaCl. The supernatant was loaded onto a 10 ml phosphocellulose (Whatman) column pre-equilibrated with buffer A containing 50 mM NaCl. The column was washed with 50 ml of loading buffer and the protein was eluted with a 80-ml total gradient of 0.05M to 0.5M NaCl in buffer A. The fractions were monitored by A280 absorption and analyzed by electrophoresis on SDS (0.1%)-polyacrylamide (12%) gels (Laemmli, Nature, 222:680-685, 1970). Proteins were stained with coomassie blue.

Restriction endonuclease activity of the fractions were assayed using pTZ19R as substrate. The fractions containing FokI were pooled and fractionated with ammonium sulfate. The 50-70% ammonium sulfate fraction contained the FokI endonuclease. The precipitate was resuspended in 50 ml of buffer A containing 25 mM NaCl and loaded onto a DEAE column. FokI does not bind to DEAE while many contaminating proteins do. The flow-through was concentrated on a phosphocellulose column. Further purification was achieved using gel filtration (AcA 44) column. The FokI was purified to electrophoretic homogeneity using this procedure.

Figure 3:
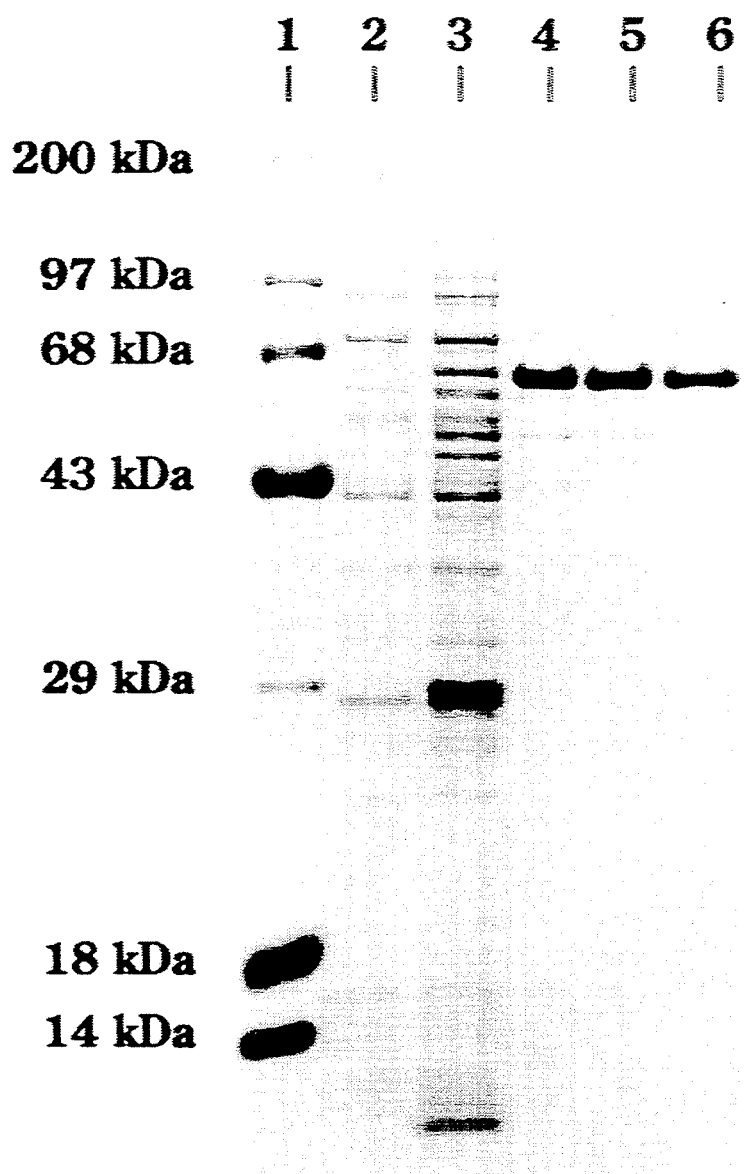
FIG. 3 shows SDS (0.1%)—polyacrylamide (12%) gel electrophoretic profiles at each step in the purification of FokI endonuclease. Lanes: 1, protein standards; 2, crude extract from uninduced cells; 3, crude extract from cells induced with 1 mM IPTG; 4, phosphocellulose pool; 5, 50–70% $(NH_4)_2SO_4$ fractionation pool; and 6, DEAE pool.

SDS (0.1%) polyacrylamide (12%) gel electrophoresis profiles of protein species present at each stage of purification are shown in FIG. 3. The sequence of the first ten amino acids of the purified enzyme was determined by protein sequencing. The determined sequence was the same as that predicted from the nucleotide sequence. Crystals of this purified enzyme have also been grown using PEG 4000 as the precipitant. FokI endonuclease was purified further using AcA44 gel filtration column.

EXAMPLE IV

Analysis of FokIR Endonuclease by Trypsin Cleavage in the Presence of DNA Substrate Trypsin is a serine protease and it cleaves at the C-terminal side of lysine and arginine residues. This is a very useful enzyme to study the domain structure of proteins and enzymes. Trypsin digestion of FokI in the presence of its substrate, d-5'-CCTCTGGATGCTCTC-3'(SEQ ID NO:10): 5'-GAGAGCATCCAGAGG-3' (SEQ ID NO:11) was carried out with an oligonucleotide duplex to FokI molar ratio of 2.5:1. FokI (200 μg) was incubated with the oligonucleotide duplex in a volume 180 μl containing 10 mM Tris.HCl, 50 mM NaCl, 10% glycerol and 10 mM $MgCl_2$ at RT for 1 hr. Trypsin (20 μl, 0.2 mg/ml) was added to the mixture. Aliquots (28 μl) from the reaction mixture were removed at different time intervals and quenched with excess trypsin inhibitor, antipain. The tryptic fragments were purified by reversed-phase HPLC and their N-terminus sequence determined using an automatic protein sequenator from Applied Biosystems.

Figure 4:
FIG. 4 shows SDS (0.1%)—polyacrylamide (12%) gel electrophoretic profiles of tryptic fragments at various time points of trypsin digestion of FokI endonuclease in presence of the oligonucleotide DNA substrate, d-5'-CCTCTGGATGCTCTC-3'(SEQ ID NO: 10): 5'-GAGAGCATCCAGAGG-3'(SEQ ID NO:11). Lanes: 1, protein standards; 2, FokI endonuclease; 3, 2.5 min; 4, 5 min; 5, 10 min; 6, 20 min; 7, 40 min; 8, 80 min; 9, 160 min of trypsin digestion respectively. Lanes 10–13: HPLC purified tryptic fragments. Lanes: 10, 41 kDa fragment; 11, 30 kDa fragment; 12, 11 kDa fragment; and 13, 25 kDa fragment.

The time course of trypsin digestion of FokI endonuclease in the presence of 2.5 molar excess of oligonucleotide substrate and 10 mM $MgCl_2$ is shown in FIG. 4. At the 2.5 min time point only two major fragments other than the intact FokI were present, a 41 kDa fragment and a 25 kDa fragment. Upon further trypsin digestion, the 41 kDa fragment degraded into a 30 kDa fragment and 11 kDA fragment. The 25 kDa fragment appeared to be resistant to any further trypsin digestion. This fragment appeared to be less stable if the trypsin digestion of FokI - oligo complex was carried out in the absence of $MgCl_2$.

Only three major fragments (30 kDa, 25 kDa and 11 kDa) were present at the 160 min time point. Each of these fragments (41 kDa, 30 kDa, 25 kDa and 11 kDa) was purified by reversed-phase HPLC and their N-terminal amino acid sequence were determined (Table I). By comparing these N-terminal sequences to the predicted sequence of FokI, the 41 kDa and 25 kDa fragments were identified as N-terminal and C-terminal fragments, respectively. In addition, the 30 kDa fragment was N-terminal.

EXAMPLE V

Isolation of DNA Binding Tryptic Fragments of FokI Endonuclease using Oligo dT-cellulose Affinity Column The DNA binding properties of the tryptic fragments were analyzed using an oligo dT-cellulose column. FokI (16.0 μg) was incubated with the 2.5 molar excess oligonucleotide duplex [d-5'-CCTCTGGATGCTCTC$(A)_{15}$-3' (SEQ ID NO:14): 5'GAGAGCATCCAGAGG$(A)_{15}$-3' (SEQ ID NO:15)] in a volume of 90 μl containing 10 mM Tris. HCl (pH 8), 50 mM NaCl, 10% glycerol and 10 mM $MgCl_2$ at RT for 1 hr. Trypsin (10 μl, 0.2 mg/ml) was added to the solution to initiate digestion. The ratio of trypsin to FokI (by weight) was 1:80. Digestion was carried out for 10 min to obtain predominantly 41 kDa N-terminal fragment and 25 kDa C-terminal fragments in the reaction mixture. The reaction was quenched with large excess of antipain (10 μg) and diluted in loading buffer [10 mM.Tris HCl (pH 8.0), 1 mM EDTA and 100 mM $MgCl_2$] to a final volume of 400 μl.

The solution was loaded onto a oligo dT-cellulose column (0.5 ml, Sigma, catalog #0-7751) pre-equilibrated with the loading buffer. The breakthrough was passed over the oligo dT-cellulose column six times. The column was washed with 5 ml of loading buffer and then eluted twice with 0.4 ml of 10 mM Tris.HCl (pH 8.0), 1 mM EDTA. These fractions contained the tryptic fragments that were bound to the oligonucleotide DNA substrate. The tryptic fragment bound to the oligo dT-cellulose column was analyzed by SDS-polyacrylamide gel electrophoresis.

In a separate reaction, the trypsin digestion was carried out for 160 min to obtain predominantly the 30 kDa, 25 kDa and 11 kDa fragments in the reaction mixture.

Figure 5:
FIG. 5 shows the identification of DNA binding tryptic fragments of FokI endonuclease using an oligo dT-cellulose column. Lanes: 1, protein standards, 2, FokI endonuclease; 3, 10 min trypsin digestion mixture of FokI - oligo complex; 4, tryptic fragments that bound to the oligo dT-cellulose column; 5, 160 min trypsin digestion mixture of FokI - oligo complex; 6, tryptic fragments that bound to the oligo dT-cellulose column.

Trypsin digestion of FokI endonuclease for 10 min yielded the 41 kDa N-terminal fragment and 25 kDa C-terminal fragments as the predominant species in the reaction mixture (FIG. 5, Lane 3). When this mixture was passed over the oligo dT-cellulose column, only the 41 kDa N-terminal fragment is retained by the column suggesting that the DNA binding property of FokI endonuclease is in the N-terminal ⅔'s of the enzyme. The 25 kDa fragment is not retained by the oligo dT-cellulose column.

Trypsin digestion of FokI - oligo complex for 160 min yielded predominantly the 30 kDa, 25 kDa and 11 kDa fragments (FIG. 5, Lane 5). When this reaction mixture was passed over oligo dT-cellulose column, only the 30 kDa and 11 kDa fragments were retained. It appears these species together bind DNA and they arise from further degradation of 41 kDa N-terminal fragment. The 25 kDa fragment was not retained by oligo dT-cellulose column. It also did not bind to DEAE and thus could be purified by passage through a DEAE column and recovering it in the breakthrough volume.

Figure 6A:
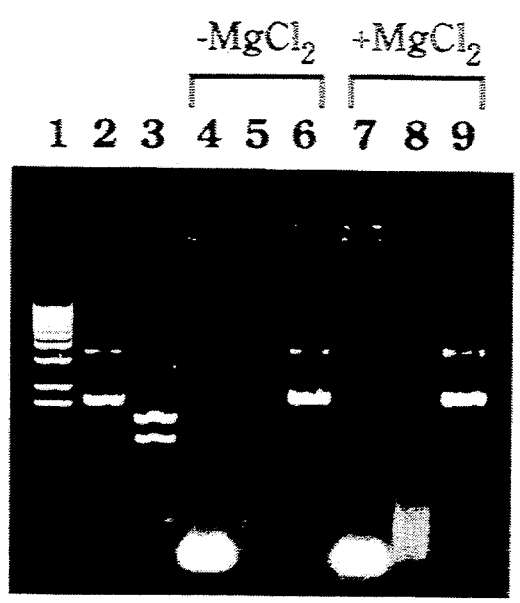
FIG. 6 shows an analysis of the cleavage properties of the tryptic fragments of FokI endonuclease.

FokI (390 μg) was incubated with 2.5 molar excess of oligonucleotide duplex [d-5'-CTCTGGATGCTCTC-3'(SEQ ID NO:10) :5'-GAGAGCATCCAGAGG-3'(SEQ ID NO:11)] in a total volume of 170 μl containing 10 mM Tris. HCl (pH 8), 50 mM NaCl and 10% glycerol at RT for 1 hr. Digestion with trypsin (30 μl; 0.2 mg/ml) in the absence of $MgCl_2$ was for 10 min at RT to maximize the yield of the 41 kDa N-terminal fragment. The reaction was quenched with excess antipain (200 μl). The tryptic digest was passed through a DEAE column. The 25 kDa of C-terminal fragment was recovered in the breakthrough volume. All the other tryptic fragments (41 kDa, 30 kDa and 11 kDa) were retained by the column and were eluted with 0.5M NaCl buffer (3×200 μl). In a separate experiment, the trypsin digestion of FokI -oligo complex was done in presence of 10 mM $MgCl_2$ at RT for 60 min to maximize the yield of 30 kDa and 11 kDa fragments. This purified fragment cleaved non-specifically both unmethylated DNA substrate (pTZ19R; FIG. 6) and methylated DNA substrate (pACYCfokIM) in the presence of $MgCl_2$. These products are small, indicating that it is relatively non-specific in cleavage. The products were dephosphorylated using calf intestinal phosphatase and rephosphorylated using polynucleotide kinase and [γ-$^{32}$P] ATP. The $^{32}$P-labeled products were digested to mononucleotides using DNase I and snake venom phosphodiesterase. Analysis of the mononucleotides by PEI-cellulose chromatography indicates that the 25 kDa fragment cleaved preferentially phosphodiester bonds 5' to G>A>>T~C. The 25 kDa C-terminal fragment thus constitutes the cleavage domain of FokI endonuclease.

The 41 kDa N-terminal fragment - oligo complex was purified by agarose gel electrophoresis. FokI endonuclease (200 μg) was incubated with 2.5 molar excess of oligonucleotide duplex, [d-5'-CCTCTGGATGCTCTC-3'(SEQ ID NO: 10): 5'-GAGAGCATCCAGAGG-3'(SEQ ID NO:11)] in a volume of 180 μl containing 10 mM Tris.HCl (pH 8.0), 50 mM NaCl and 10% glycerol at RT for 1 hr. Tracer amounts of $^{32}$P-labeled oligonucleotide duplex was incorporated into the complex to monitor it during gel electrophoresis. Digestion with trypsin (20 μl; 0.2 mg/ml) was for 12 min at RT to maximize the yield of the 41 kDa N-terminal fragment. The reaction was quenched with excess antipain. The 41 kDa N-terminal fragment - oligo complex was purified by agarose gel electrophoresis. The band corresponding to the complex was excised and recovered by electroelution in a dialysis bag (~600 μl). Analysis of the complex by SDS~PAGE revealed 41 kDa N-terminal fragment to be the major component. The 30 kDa N-terminal fragment and the 11 kDa C-terminal fragment were present as minor components. These together appeared to bind DNA and co-migrate with the 41 kDa N-terminal fragment-oligo complex.

The binding specificity of the 41 KDa N-terminal fragment was determined using gel mobility shift assays.

EXAMPLE VI

Gel Mobility Shift Assays

The specific oligos (d-5'-CCTCTGGATGCTCTC-3'(SEQ ID NO: 10) and d-5'-GAGAGCATC-CAGAGG-3' (SEQ ID NO: 11) ) were 5'-$^{32}$P-labeled in a reaction mixture of 25 μl containing 40 mM Tris.HCl(pH7.5), 20 mM MgCl$_2$,50 mM NaCl, 10 mM DTT, 10 units of T4 polynucleotide kinase ( from New England Biolabs ) and 20 μCi[λ-$^{32}$P] ATP (3000 Ci/mmol). The mixture was incubated at 37° C. for 30 min. The kinase was inactivated by heating the reaction mixture to 70° C. for 15 min. After addition of 200 μl of water, the solution was passed through Sephadex G-25 (Superfine) column (Pharmacia) to remove the unreacted [λ-$^{32}$P] ATP. The final concentration of labeled single-strand oligos were 27 μM.

The single-strands were then annealed to form the duplex in 10 mM Tris.HCl (pH 8.0), 50 mM NaCl to a concentration of 12 μM. 1 μl of the solution contained ~12 picomoles of oligo duplex and ~50×10$^3$cpm. The non-specific oligos (d-5'-TAATTGATTCTTAA-3'(SEQ ID NO:12) and d-5'-ATTAAGAATCAATT-3'(SEQ ID NO:13)) were labeled with [λ-$^{32}$P]ATP and polynucleotide kinase as described herein. The single-stranded oligos were annealed to yield the duplex at a concentration of 12 μM. 1 μl of the solution contained ~12 picomoles of oligo duplex and ~25×10$^3$cpm. The non-specific oligos (d-5'-TAATTGATTCTTAA-3'(SEQ ID NO:12) and d-5'-ATTAAGAATCAATT-3'(SEQ ID NO:13)) were labeled with [λ-$^{32}$P] ATP and polynucleotide Kinase as described herein. The single-strand oligos were annealed to yield the duplex at a concentration of 12 μM. 1 μl of the solution contained 42 picomdes of oligo duplex and ~25×10$^3$ cpm.

10 μl of 41 kDa N-terminal fragment-oligo complex (~2 pmoles) in 10 mM Tris.HCl, 50 mM NaCl and 10 mM MgCl$_2$ was incubated with 1 μl of $^{32}$P-labeled specific oligonucleotide duplex (or $^{32}$P-labeled non-specific oligonucleotide duplex) at 37° C. for 30 min and 120 min respectively. 5 μl of 75% glycerol was added to each sample and loaded on a 8% nondenaturing polyacrylamide gel. Electrophoresis was at 300 volts in TBE buffer until bromophenol blue moved ~6 cm from the top of the gel. The gel was dried and autoradiographed.

The complex readily exchanged $^{32}$P-labeled specific oligonucleotide duplex that contained the FokI recognition site as seen from the gel mobility shift assays (FIG. 7). It did not, however, exchange the $^{32}$P-labeled non-specific oligonucleotide duplex that did not contain the FokI recognition site. These results indicate that all the information necessary for sequence-specific recognition of DNA are encoded within the 41 kDa N-terminal fragment of FokI.

EXAMPLE VII

Analysis of FokI by Trypsin Cleavage in the Absence of DNA Substrate

A time course of trypsin digestion of FokI endonuclease in the absence of the DNA substrate is shown in FIG. 8. Initially, FokI cleaved into a 58 kDa fragment and a 8 kDa fragment. The 58 kDa fragment did not bind DNA substrates and is not retained by the oligo dT-cellulose column. On further digestion, the 58 kDa fragment degraded into several intermediate tryptic fragments. However, the complete trypsin digestion yielded only 25 kDa fragments (appears as two overlapping bands).

Each of these species (58 kDa, 25 kDa and 8 kDa) were purified by reversed phase HPLC and their amino terminal amino acid sequence determined (Table I). Comparison of the N-terminal sequences to the predicted FokI sequence revealed that the 8 kDa fragment to be N-terminal and the 58 kDa fragment to be C-terminal. This further supports the conclusion that N-terminus of FokI is responsible for the recognition domain. Sequencing the N-terminus of the 25 kDa fragments revealed the presence of two different components. A time course of trypsin digestion of FokI endonuclease in a the presence of a non-specific DNA substrate yielded a profile similar to the one obtained when trypsin digestion of FokI is carried out in absence of any DNA substrate.

EXAMPLE VIII

Cleavage Specificity of the 25 kDa C-terminal Tryptic Fragment of FokI

The 25 kDa C-terminal tryptic fragment of FokI cleaved pTZ19R to small products indicating non-specific cleavage. The degradation products were dephosphorylated by calf intestinal phosphatase and $^{32}$P-labeled with the polynucleotide kinase and [λ-$^{32}$P]ATP. The excess label was removed using a Sephadex G-25 (Superfine) column. The labeled products were then digested with 1 unit of pancreatic DNase I (Boehringer-Mannheim) in buffer containing 50 mM Tris. HCl(pH7.6), 10 mM MgCl$_2$ at 37° C. for 1 hr. Then, 0.02 units of snake venom phosphodiesterase was added to the reaction mixture and digested at 37° C. for 1 hr.

EXAMPLE IX

Functional Domains in FokI Restriction Endonuclease

Analysis of functional domains of FokI (in the presence and absence of substrates) using trypsin was summarized in FIG. 9. Binding of DNA substrate by FokI was accompanied by alteration in the structure of the enzyme. This study supports that presence of two separate protein domains within this enzyme: one for sequence-specific recognition and the other for endonuclease activity. The results indicate that the recognition domain is at the N-terminus of the FokI endonuclease, while the cleavage domain is probably in the C-terminus third of the molecule.

Examples Relating to Construction of Insertion Mutants (X-XIV)

The complete nucleotide sequence of the FokI RM system has been published by various laboratories (Looney et al., Gene 80: 193-208, 1989 & Kita et al., J. Biol. Chem. 264: 5751-56, 1989). Experimental protocols for PCR are described, for example, in Skoglund et al., Gene 88:1-5, 1990 and in Bassing et al., Gene 113:83-88, 1992. The procedures for cell growth and purification of the mutant enzymes are similar to the ones used for the wild-type FokI (Li et al., Proc. Nat'l. Acad. Sci. USA 89:4275-79, 1992). Additional steps which include Sephadex G-75 gel filtration and Heparin-Sepharose CL-6B column chromatography were necessary to purify the mutant enzymes to homogeneity.

EXAMPLE X

Mutagensis of SpeI Site at Nucleotide 162 within the fokIR Gene

The two step PCR technique used to mutagenize one of the SpeI sites within the fokIR gene is described in Landt et al., Gene 96: 125-28, 1990. The three synthetic primers for this protocol include: 1) the mutagenic primer (5'-TCATAA TAGCAACTAATTCTTTTT-GGATCTT-3') (see SEQ ID NO:24) containing one base mismatch within the SpeI site; 2) the other primers each of which are flanked by restriction sites ClaI (5'-CCATCGATATAGCCTTTTTTATT-3') (see SEQ ID N0:25) and XbaI (5'-GCTCTAGAGGATCC-GGAGGT-3') (see SEQ ID NO:26), respectively. An intermediate fragment was amplified using the XbaI primer and the mutagenic primer during the first step. The ClaI primer was then added to the intermediate for the second step PCR. The final 0.3 kb PCR product was digested with XbaI/ClaI to generate cohesive ends and gel-purified. The expression vector (pRRSfokIR) was cleaved with XbaI/ClaI. The large 4.2 kb fragment was then gel-purified and ligated to the PCR fragment. The recombinant DNA was transfected into competent E. coli RR1[pACYCfokIM] cells. After tetracycline and ampicillin antibiotic selection several clones were picked, and their plasmid DNA was examined by restriction analysis. The SpeI site mutation was confirmed by sequencing the plasmid DNA using Sanger's sequencing method (Sanger et al. Proc. Natl. Acad. Sci. USA 74: 5463-67, 1977).

EXAMPLE XI

Construction of Four (or Seven) Codon Insertion Mutants

The PCR-generated DNA containing a four (or seven) codon insertion was digested with a SpeI/XmaI and gel-purified. The plasmid, pRRSfokIR from Example X was cleaved with SpeI/XmaI, and the large 3.9 kb fragment was gel-purified and ligated to the PCR product. The recombinant DNA was transfected into competent RR1[pACYCfokIM] cells, and the desired clones identified as described in Example X. The plasmids from these clones were isolated and sequenced to confirm the presence of the four (or seven) codon insertion within the fokIR gene.

In particular, the construction of the mutants was performed as follows: (1) There are two SpeI sites at nucleotides 162 and 1152, respectively, within the fokIR gene sequence. The site at 1152 is located near the trypsin cleavage site of FokI that separates the recognition and cleavage domains. In order to insert the four (or seven) codons around this region, the other SpeI site at 162 was mutagenized using a two step PCR technique (Landt et al. Gene 96:125-28, 1990). Introduction of this SpeI site mutation in the fokIR gene does not affect the expression levels of the overproducer clones. (2) The insertion of four (or seven) codons was achieved using the PCR technique. The mutagenic primers used in the PCR amplification are shown in FIG. 11. Each primer has a 21 bp complementary sequence to the fokIR gene. The 5' end of these primers are flanked by SpeI sites. The codons for KSEL and KSELEEK repeats are incorporated between the SpeI site and the 21 bp complement. Degenerate codons were used in these repeats to circumvent potential problems during PCR amplification. The other primer is complementary to the 3' end of the fokIR gene and is flanked by a XmaI site. The PCR-generated 0.6 kb fragments containing the four (or seven) codon inserts digested with SpeI/XmaI and gel-purified. These fragments were substituted into the high expression vector pRRSfokIR to generate the mutants. Several clones of each mutant identified and their DNA sequence confirmed by Sanger's dideoxy chain termination method (Sanger et al. Proc. Natl. Acad. Sci. USA 74.5463-67 1977).

Upon induction with 1 mM isopropyl $\beta$-D-thiogalactoside (IPTG), the expression of mutant enzymes in these clones became most prominent at 3 hrs as determined by SDS/PAGE. This was further supported by the assays for the enzyme activity. The levels of expression of the mutant enzymes in these clones were much lower compared to the wild-type FokI. IPTG induction for longer times resulted in lower enzyme levels indicating that the mutant enzymes were actively degraded within these clones. This suggests that the insertion of four (or seven) codons between the recognition and cleavage domains of FokI destabilizes the protein conformation making them more susceptible to degradation within the cells. SDS/PAGE profiles of the mutant enzymes are shown in FIG. 12.

EXAMPLE XII

Preparation of DNA Substrates with a Single FokI Site

Two substrates, each containing a single FokI recognition site, were prepared by PCR using pTZ19R as the template. Oligonucleotide primers, 5'-CGCAGTGT-TATCACTCAT-3' and 5'-CTTGGTTGAGTACT-CACC-3' (see SEQ ID N0:27 and SEQ ID NO:28, respectively), were used to synthesize the 100 bp fragment. Primers, 5'-ACCGAGCTCGAATTCACT-3' and 5'-GATTTCGGCCTATTGGTT-3' (see SEQ ID NO:29 and SEQ ID NO:30, respectively), were used to prepare the 256 bp fragment. Individual strands within these substrates were radiolabeled by using the corresponding $^{32}$P-labeled phosphorylated primers during PCR. The products were purified from low-melting agarose gel, ethanol precipitated and resuspended in TE buffer.

EXAMPLE XIII

Analysis of the Sequence Specificity of the Mutant Enzymes

Figure 13A:
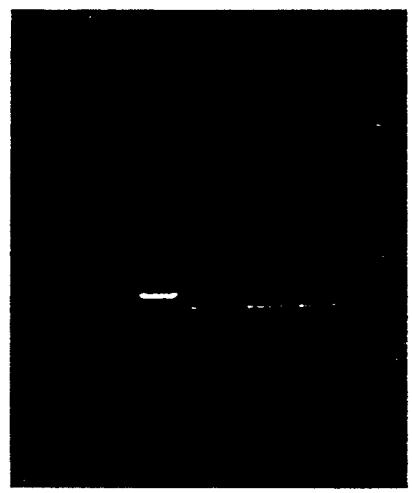
Figure 13B:
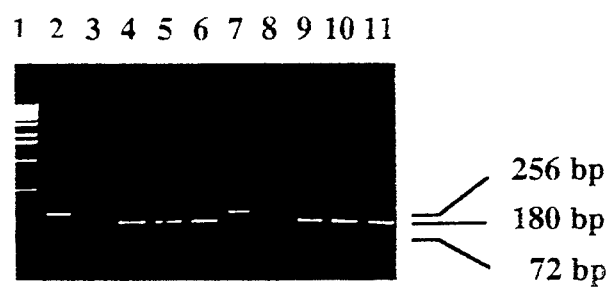
Figure 13C:
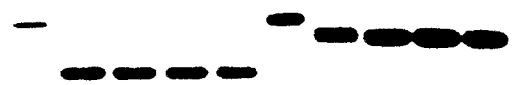

The agarose gel electrophoretic profile of the cleavage products of pTZ19R DNA by FokI and the mutants are shown in FIG. 13A. They are very similar suggesting that insertion of four (or seven) codons in the linker region between the recognition and cleavage domains does not alter its DNA sequence specificity. This was further confirmed by using $^{32}$P-labeled DNA substrates (100 bp and 256 bp) each containing a single FokI site. Substrates containing individual strands labeled with $^{32}$p were prepared as described in Example XII. FokI cleaves the 256 bp substrate into two fragments, 180 bp and 72 bp, respectively (FIG. 13B). The length of the fragments was calculated from the $^{32}$P-labeled 5' end of each strand. The autoradiograph of the agarose gel is shown in FIG. 13C. Depending on which strand carries the $^{32}$P-label in the substrate, either 72 bp fragment or 180 bp fragment appears as a band in the autoradiograph. The mutant enzymes reveal identical agarose gel profiles and autoradiograph. Therefore, insertion of four (or seven) codons between the recognition and cleavage domains does not alter the DNA recognition mechanism of FokI endonuclease.

EXAMPLE XIV

Figure 14A:
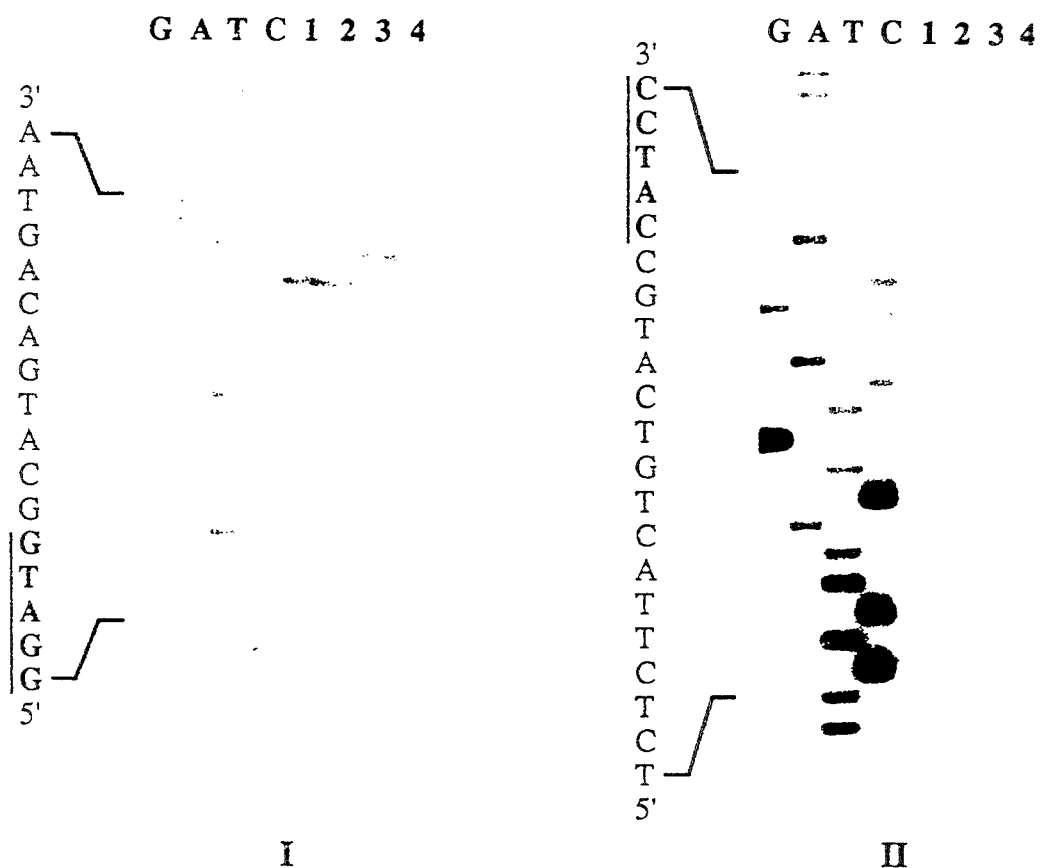

Analysis of the Cleavage Distances from the Recognition Site by the Mutant Enzymes To determine the distance of cleavage by the mutant enzymes, their cleavage products of the $^{32}$P-labeled substrates were analyzed by PAGE (FIG. 14). The digests were analyzed alongside the sequencing reactions of pTZ19R performed with the same primers used in PCR to synthesize these substrates. The cleavage pattern of the 100 bp fragment by FokI and the mutants are shown in FIG. 14A. The cut sites are shifted from the recognition site on both strands of the substrates in the case of the mutants, as compared to the wild-type enzyme. The small observable shifts between the sequencing gel and the cleavage products are due to the unphosphorylated primers that were used in the sequencing reactions.

On the 5'-GGATG-3' strand, both mutants cut the DNA 10 nucleotides away from the site while on the 5'-CATCC-3' strand they cut 14 nucleotides away from the recognition site. These appear to be the major cut sites for both the mutants. A small amount of cleavage similar to the wild-type enzyme was is also observed.

The cleavage pattern of the 256 bp fragment is shown in FIG. 14B. The pattern of cleavage is shown in FIG. 14B. The pattern of cleavage is similar to the 100 bp fragment. Some cleavage is seen 15 nucleotides away from the recognition site on the 5'-CATCC-3' strand in the case of the mutants. The multiple cut sites for the mutant enzymes could be attributed to the presence of different conformations in these proteins. Or due to the increased flexibility of the spacer region between the two domains. Depending on the DNA substrate, some variation in the intensity of cleavage at these sites was observed. This may be due to the nucleotide sequence around these cut sites. Naturally occurring Type IIS enzymes with multiple cut sites have been reported (Szybalski et al., *Gene* 100:13-26, 1991).

Examples Relating to Construction of the Hybrid Enzyme Ubx-F$_N$ (XV-XVII)

As noted above, the complete nucleotide sequence of the FokI restriction-modification system has been published by other laboratories (Kita et al., *J. Biol Chem.* 264: 5751-56 (1989); Looney et al., *Gene* 80:193-208 (1989)). Experimental protocols for PCR are described elsewhere (Skoglund et al., *Gene* 88:1-5 (1990)). The procedures for cell growth and purification of proteins using Hisbind TM resin is as outlined in Novagen pET system manual. Additional steps, which include phosphocellulose and DEAE column chromatography, were necessary to purify the hybrid protein, Ubx-F$_N$. to near homogeneity. The protocol for SDS/PAGE is as described by Laemmli (Nature 222:680-685 (1970)).

Preparation of pUC13 Derived Substrates pUC13 derived DNA substrates were prepared by blunt-end ligation of SmaI-cleaved pUC13 plasmid with ten-fold excess of a 30 bp insert containing a known Ubx site, 5'-TTAATGGTT-3'. Several clones were picked and their plasmid DNA were analyzed for the presence of 30 bp inserts. Clones containing pUC13(1), pUC13(2) or pUC13(3), each with 1, 2 and 3 inserts respectively, were identified. Their DNA sequences were confirmed by Sanger's dideoxy sequencing method (*Proc. Natl. Acad. Sci. USA* 74:5463-67 (1977).

Preparation of DNA Substrates with a Single Ubx Site

The polylinker region of pUC13(1) which has a single 30 bp insert was excised using EcoRI/HindIII and gel-purified. Individual stands of his substrate were radiolabeled by using $^{32}$P-dATP or $^{32}$P-dCTP and filling in the sticky ends of the fragment with Klenow enzyme. The products were purified from low-melting agarose gel, ethanol-precipitated, and resuspended in the buffer (10 mM Tris. HCl/1 mM EDTA, pH 8.0).

EXAMPLE XV

Construction of the Clone Producing the Hybrid Enzyme, Ubx-F$_N$ Using PCR

The homeo domain of Ubx, a 61 amino acid protein sequence encoded by the homeobox of Ubx is a sequence-specific DNA-binding domain with a structure related to helix-turn-helix motifs found in bacterial DNA-binding proteins (Hayashi et al., *Cell* 63:883-94 (1992); Wolberger et al., *Cell* 7:517-28 (1991). The Ubx homeo domain recognizes the 9 bp consensus DNA sites, 5'-TTAAT (G/T) (G/A) CC-3' (Ekker et al., *The EMBO Journal* 10:1179-86 (1991); Ekker et al., *The EMBO Journal* 11:4059-4702 (1992)). The present inventors used the PCR technique to link the Ubx homeo domain to the cleavage domain (F.) of FokI and to express the Ubx-F$_N$ enzyme in *E. coli.* A schematic representation of the engineered Ubx-F$_N$ hybrid protein is shown in FIG. 16. The oligonucleotide primers used to construct the hybrid gene is shown in FIG. 17A.

Figure 17B:
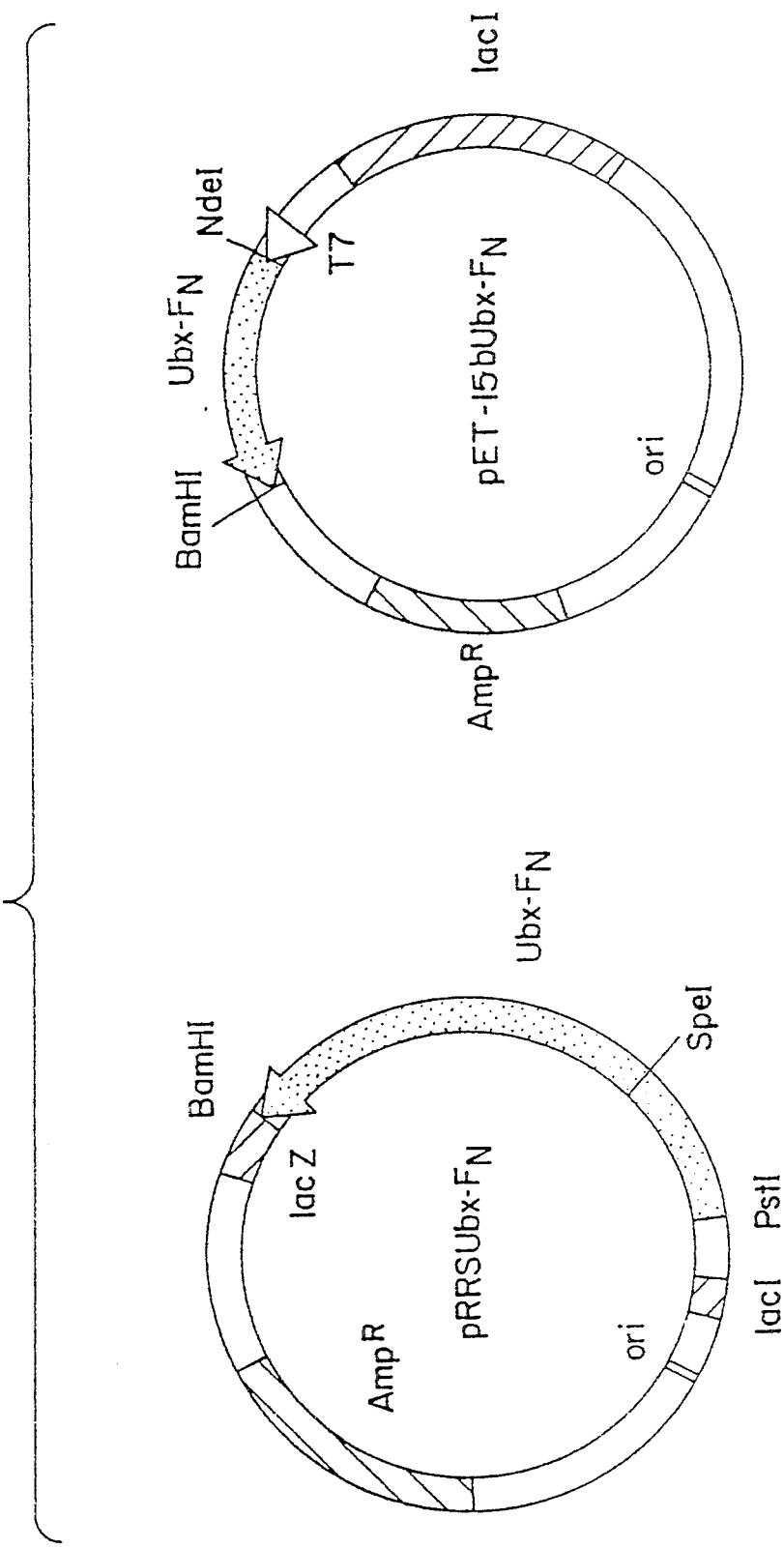

Construction of the clone expressing the hybrid protein was done as follows: First, the PCR-generated Ubx homeo box was digested with PstI/SpeI and gel-purified. This fragment was then substituted into the vector pRRSfokIR to replace the DNA segment coding for the FokI DNA-binding domain and, hence, form the Ubx-F$_N$ hybrid gene (FIG. 17B). After transfection of competent RR1 cells with the ligation mix, several clones were identified by restriction analysis and their DNA sequences were confirmed by the dideoxy chain-termination method of Sanger et al. (*Proc. Natl. Acad. Sci. USA* 74:5463-67 (1977)). Second, the hybrid gene was amplified using the Ubx-$F_N$ primers. The PCR-generated DNA was digested with NdeI/BamHI and gel-purified. This fragment was then ligated into the NdeI/BamHI-cleaved pET-15b vector. This construct will tag the hybrid protein with 6 consecutive histidine residues at the N-terminus. These serve as the affinity tag for purification of this protein by metal chelation chromatography using Novagen's His-bind ™ resin. This His tag can be subsequently removed by thrombin. Competent BL21(DE3) cells were transformed with the ligation mix and several clones containing the recombinant DNA (FIG. 17B) were identified. These colonies were sick and grew poorly in culture with a doubling time of about 45 minutes. After induction with 1 mM isopropyl-β-D-thiagalactoside (IPTG), the hybrid enzyme was purified to homogeneity using His-bind ™ resin, phosphocellulose and gel-chromatography. The SDS/PAGE profile of the purified hybrid enzyme is shown in FIG. 18. The identity of the hybrid protein was further confirmed by probing the Western blot with rabbit antisera raised against FokI endonuclease (data not shown).

EXAMPLE XVI

Analysis of the DNA Sequence Preference of the Ubx-$F_N$ Hybrid Enzyme

The linearized pUC13 derived substrates used to characterize Ubx-$F_N$ are shown in FIG. 19. The derivatives were constructed by inserting a 30 bp DNA fragment containing a known Ubx recognition sequence 5'-TTAATGGTT-3' at the SmaI site of pUC13. Cleavage at the inserted Ubx site should yield ~1.8 kb and ~0.95 kb fragments as products. The agarose gel electrophoretic profile of the partial digests of the substrates by Ubx-$F_N$ is shown in FIG. 19. In these reactions, the molar ratio of DNA was in large excess compared to the protein. The reaction condition was optimized to give a single double-stranded cleavage per substrate molecule. The linearized pUC13 DNA is cleaved into four fragments. The appearance of four distinct bands in the agarose gel electrophoretic profile indicates that Ubx-$F_N$ binds DNA in a sequence-specific manner, and that there are two binding sites within the linearized pUC13 for the hybrid protein. This is further supported by the fact that the linearized pUC13 DNA substrate containing a single Ubx site is cleaved into six fragments. The two additional fragments (~1.8 kb and ~0.95 kb, respectively) could be explained as resulting from the binding of the hybrid protein at the newly inserted Ubx site of pUC13 and cleaving near this site. As expected, the intensity of the bands increases with the number of 30 bp inserts in pUC13. The two Putative Ubx binding sites in pUC13 and the inserted Ubx site are shown in Table 3 below. All these sites have 5'-TAAT-3' as their core sequence; and these preferred sites are consistent with those reported for the Ubx homeo domain. The affinity of Ubx homeo domain for these sites is modulated by the nucleotide bases surrounding the core site. It appears that the hybrid protein does turn-over, since complete digestion is observed at longer time period or by increasing the protein concentration (data not shown). The cleavage is more specific at higher temperatures.

EXAMPLE XVII

Analysis of the Cleavage Distance from the Recognition Site by the Hybrid Enzyme To determine the distance of cleavage from the recognition site by Ubx-$F_N$, the cleavage products of the $^{32}$P-labeled DNA substrates containing a single Ubx site were analyzed by PAGE (FIG. 20). The digestion products were analyzed alongside the Maxam-Gilbert's (G+A) sequencing reactions of the substrates. As expected, the cut sites are shifted away from the recognition site. On the 5'-TAAT-3' strand, Ubx-$F_N$ cuts the DNA 3 nucleotides away from the recognition site while on the 5'-ATTA-3' strand it cuts 8, 9 or 10 nucleotide away from the recognition site. Analysis of the cut sites of Ubx-$F_N$ based on the cleavage of the DNA substrate containing a single Ubx site is summarized in FIG. 20. The cleavage occurs 5' to the TAAT sequence and is consistent with the way the Ubx-$F_N$ hybrid protein was engineered (FIG. 16).

TABLE 1

| | Amino-terminal sequences of FokI fragments from trypsin digestion | | |
|---|---|---|---|
| Fragment | Amino-terminal sequence | DNA substrate | SEQ ID NO |
| 8 kDa | VSKIRTFG*VQNPGKFENLKRVVQVFDRS | — | 16 |
| 58 kDa | SEAPCDAIIQ | | 17 |
| 25 kDa | QLVKSELEEK | + | 18 |
| 41 kDa | VSKIRTFGWV | | 19 |
| 30 kDa | VSKIRTFGWV | | 19 |
| 11 kDa | FTRVPKRVY | | 20 |

TABLE 2

| No. (1) | ENase-IIS[a] (isoschizomers) (2) | Protruding ends[c] (5) | Species (strain)[d] (6) | Co-produced ENases[e] (7) | Described MTases-II[f] [C or A] (8) | Commercial availability[g] (9) | References (10) |
|---|---|---|---|---|---|---|---|
| 1. | AlwI (BinI) ((BthII)[i] | 5'N$_1$ | Acinetobacter lwofii | | | N,Z | Mo2, Ne3 |
| 2. | AlwXI (BbvI) | 5'N$_4$ | Acinetobacter lwofii X | | (M·BbvI) [C-5] | | Mo6 |
| 3. | Alw26I (BsmAI) | 5'N$_4$ | Acinetobacter lwofii RFL26 | | M-Alw26I [C-5 and A-N6] | | G11, Bi2 |
| 4. | BbsI (BbvII) | 5'N$_4$ | *Bacillus brevis* (laterosporus | | | N | Mo2, Ne3 |

TABLE 2-continued

| No. (1) | ENase-IIS[a] (isoschizomers) (2) | Protruding ends[c] (5) | Species (strain)[d] (6) | Co-produced ENases[c] (7) | Described MTases-II[f] [C or A] (8) | Commercial availability[g] (9) | References (10) |
|---|---|---|---|---|---|---|---|
| 5. | BbvI (AlwXI) (Uba1109I)[j] (Bsp432I) | 5'N$_4$ | Bacillus brevis (ATCC 9999) NEB573) | BbvII | M·BbvI [C-5] | G,I,N,Z | Ba4, Do1, Do2, Gi2, Gi3, Ha4, Ha5, Ne3, Sc2, Va1 |
| 6. | BbvII (Bbv16I)[j] (BspVI) | 5'N$_4$ | Bacillus brevis 80 | BbvI | | | Bu1, Bu2, Do2, Ma4 |
| 7. | BcefI | 5'N$_1$ | Bacillus cereus subsp. flourescens | | | | Ve1, Ve2 |
| 8. | BccI | | Bacteroides caccae | | | (N) | Mo2 |
| 9. | BcgI | 3'N$_2$ 3'N$_2$ | Bacillus coagulans (NEB 566) | | | N | H. Kong, No3 |
| 10. | BinI (AlwI) (BthII)[j] | 5'N$_1$ | Bifidobacterium infantis | | | N | Bo2, Kh1, Kh2 |
| 11. | BsaI (Eco31I)[j] | 5'N$_4$ | Bacillus stearothermophilus 6-55 | | | N | H. Kong, Mo2, Ne3 |
| 12. | BsgI | 3'N$_2$ | Bacillus sphaericus GC | | | N | Sc2 |
| 13. | BsmAI (Alw26I) | 5'N$_4$ | Bacillus stearothermophilus A664 (NEB 481) | | | N | Ch1, Ko1, Ne3 |
| 14. | BspMI | 5'N$_4$ | Bacillus species M (NEB 356) | BspMII | We3 | N | Ha1, Ki2, Ki4, Ku1, Mc2, Mo2, Mo4, Mo7 |
| 15. | EarI (Ksp632I) | 5'N$_3$ | Enterobacter aerogenes (NEB 450) | | | N | Ne3, Po3 |
| 16. | Eco31I (BsaI)[j] | 5'N$_4$ | Escherichia coli RFL31 | | M·Eco31I [C-5] and [A-N6] | F | Bi2, Bu3 |
| 17. | Eco57I (Bsp6II)[j] (Eco112I)[j] (Eco125I)[j] (FsfI)[j] | 3'N$_2$ | Escherichia coli RFL57$_1$ | | M·Eco57I [A-N6] | F,N | Ja2, Ja3, Pe1, Pe2 |
| 18. | Esp3I | 5'N$_4$ | Erwinia sp RFL3 | | M·Esp3I [C-5, A-N6] | F,N | Bi2 |
| 19. | FauI | 5'N$_2$ | Flavobacterium aquatili | | | | De1 |
| 20. | FokI (HinGuII) | 5'N$_4$ | Flavobacterium okeanokoites | | M·FokI [A-N6] | A,M,N,S,U,Z | Ba4, Ha2, Ha3, Ka1, Ka2, Ki1, Ki3, Ki4, Ki5, Ki6, Ki7, Kr1, La1, Lo1, Lu1, Ma1, Ma3, Mc1, Ne3, Nw1, Po1, Po4, Po5, P06, Sc3, sc4, sk1, su2, Su3, Su4, Sz1, Ve3, Ve4, Wi1 |
| 21. | GsuI (Bco35I)[j] (Bsp22I)[j] (Bsp28I)[j] | 3'N$_2$ | Gluconobacter dioxyacetonicus H-15T | | M·GsuI | F,N | Bi1, Ja1, Pe1, Pe2 |
| 22. | HgaI | 5'N$_5$ | Haemophilus gallinarum (ATCC14385) | | M·HgaI (two MTases) [C-5] | N,Z | Ba4, Br1, Br6, Ko4, Kr1, Mo8, Ne1, Ne3, Su1, Ta1, To1, Ur1 |
| 23. | HinGuII (FokI) | 5'N$_4$ | Haemophilus infuenzae GU | | | | Na2 |
| 24. | HphI (NgoVII) (NgoBI)[j] | 3'N$_1$ (or blunt) | Haemophilus parahaemolyticus | | M·HphI [A-N6] | N,Z | Ba1, Co1, Kl1, Ne2, Ne3, Ro1 |
| 25. | Ksp632I (EarI) (BsrEI)[j] | 5'N$_3$ | Kluyvera sp. 632 | | | M | Bo1 |
| 26. | MboII (NcuI)[j] (TceI)[j] | 3'N$_1$ | Moraxella bovis (ATCC10900) | MboI | M·MboII [A-N6] | B,G,I,N,P,U,Z | Ba1, Br3, Br5, En1, Ga1, Ge1, Ha2, Mc1, Mc3, Na1, Na2, Ne2, Ne3, Sc1, Se1, Sm1 |
| 27. | MmeI | 3'N$_2$ | Methylophilus methyltrophus | MmeII | | U | Bo3, Tu1 |
| 28. | MnlI | 3'N$_1$ | Moraxella nonliquefaciens (ATCC17953) | | | I,N,S,Z | Br2, Ne3, Sc2, Vi1, Ea1 |

TABLE 2-continued

| No. (1) | ENase-IIS[a] (isoschizomers) (2) | Protruding ends[c] (5) | Species (strain)[d] (6) | Co-produced ENases[c] (7) | Described MTases-II[f] [C or A] (8) | Commercial availability[g] (9) | References (10) |
|---|---|---|---|---|---|---|---|
| 29. | NgoVIII (HphI) | n.d. | Neisseria gonorrhoeae | | M-NgoVIII | | Ko2 |
| 30. | PleI | 5'$N_1$ | Pseudomonas lemoignei (NEB418) | | | N | Mo6, Me3 |
| 31. | RleAI | 3'$N_3$ | Rhizobium leguminosarum | | | | Ve5 |
| 32. | SapI | 5'$N_3$ | Saccharopolyspora sp. | | | N | Mo2, Ne3 |
| 33. | SfaNI (BscAI)[i] | 5'$N_4$ | Streptococcus faecalis ND547 | | M-SfaI | N,Z | Ba4, Ne3, Po5, Po6, Sc2, Sc3, Sc5, Sp1 |
| 34. | TaqII | 3'$N_2$ | Thermus aquaticus | TaqI | | U | Ba2, My1 |
| 35. | Tth111II | 3'$N_2$ | Thermus thermophilus 111 | Tth111I | | Y,Z | Sh1, Sh2 |
| 36. | Sts I | | Streptococcus sanguis 54 | | | | |
| Related ENases:[h] | | | | | | | |
| 36. | BsmI (Asp35HI)[k] | 3'$N_1$ | Bacillus stearothermophilus NUB36 | | | N | Gi1, Ha6, In1, M07, My1, Ne3, Pa1, |
| 37. | BarI (BarSI) | 3'$N_1$ | Bacillus stearothermophilus (NEB447) | | | N | Ne3, Po2 | from Szybalski et al. [GENE 100:13–26 (1991)]

TABLE 3

Ubx-binding Sites in pUC13

| Sequence | Remarks |
|---|---|
| 5'-TTAATGTCA-3' | putative Ubx sites present in pUC13 |
| 5'-TTAATGAAT-3' | |
| 5'-TTAATGGTT-3' | Ubx site inserted at the SmaI site of pUC13 |

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGATG      5

( 2 ) INFORMATION FOR SEQ ID NO:2:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

C C T A C      5

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 18..35

( x i ) SEQUENCE DESCRIPTION: SEQ ID NO:3:

```
CCATGGAGGT TTAAAAT ATG AGA TTT ATT GGC AGC                    35
                   Met Arg Phe Ile Gly Ser
                    1               5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Arg Phe Ile Gly Ser
 1               5
```

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
ATACCATGGG AATTAAATGA CACAGCATCA                              30
```

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 22..42

( x i ) SEQUENCE DESCRIPTION: SEQ ID NO:6:

```
TAGGATCCGG AGGTTTAAAA T ATG GTT TCT AAA ATA AGA ACT           42
                       Met Val Ser Lys Ile Arg Thr
                        1               5
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Met Val Ser Lys Ile Arg Thr
1               5

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TAGGATCCTC ATTAAAGTT TATCTCGCCG TTATT        35

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

Asn Asn Gly Glu Ile Asn Phe
1               5

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CCTCTGGATG CTCTC        15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GAGAGCATCC AGAGG        15

( 2 ) INFORMATION FOR SEQ ID NO:12:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TAATTGATTC TTAA        14

( 2 ) INFORMATION FOR SEQ ID NO:13:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

ATTAAGAATC AATT                                                                14

( 2 ) INFORMATION FOR SEQ ID NO:14:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

CCTCTGGATG CTCTCAAAAA AAAAAAAAAA                                                30

( 2 ) INFORMATION FOR SEQ ID NO:15:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

GAGAGCATCC AGAGGAAAAA AAAAAAAAAA                                                30

( 2 ) INFORMATION FOR SEQ ID NO:16:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:16:

Val Ser Lys Ile Arg Thr Phe Gly Xaa Val Gln Asn Pro Gly Lys
1               5                   10                  15

Phe Glu Asn Leu Lys Arg Val Val Gln Val Phe Asp Arg Ser
                    20                  25

( 2 ) INFORMATION FOR SEQ ID NO:17:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:17:

Ser Glu Ala Pro Cys Asp Ala Ile Ile Gln
    1               5                   10

( 2 ) INFORMATION FOR SEQ ID NO:18:

( i ) SEQUENCE CHARACTERISTICS:
    ( A ) LENGTH: 10 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Gln Leu Val Lys Ser Glu Leu Glu Glu Lys
    1               5                   10

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Val Ser Lys Ile Arg Thr Phe Gly Trp Val
    1               5                   10

(2) INFORMATION FOR SEQ ID NO:20:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Phe Thr Arg Val Pro Lys Arg Val Tyr
    1               5

(2) INFORMATION FOR SEQ ID NO:21:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Glu Glu Lys
    1

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Lys Ser Glu Leu
    1

(2) INFORMATION FOR SEQ ID NO:23:

(i) SEQUENCE CHARACTERISTICS:
        (A) LENGTH: 7 amino acids
        (B) TYPE: amino acid
        (C) STRANDEDNESS: single -continued (D) TOPOLOGY: linear (ii) MOLECULE TYPE: peptide (xi) SEQUENCE DESCRIPTION: SEQ ID NO:23:

Lys Ser Glu Leu Glu Glu Lys
1               5

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TAGCAACTAA TTCTTTTTGG ATCTT  25

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CCATCGATAT AGCCTTTTTT ATT  23

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GCTCTAGAGG ATCCGGAGGT  20

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CGCAGTGTTA TCACTCAT  18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CTTGGTTGAG TACTCACC                                                       18

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

ACCGAGCTCG AATTCACT                                                       18

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GATTTCGGCC TATTGGTT                                                       18

( 2 ) INFORMATION FOR SEQ ID NO:31:

( i ) SEQUENCE CHARACTERISTICS:
        ( A ) LENGTH: 579 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Met Val Ser Lys Ile Arg Thr Phe Gly Trp Val Gln Asn Pro Gly
 1               5                  10                  15

Lys Phe Glu Asn Leu Lys Arg Val Val Gln Val Phe Asp Arg Asn
                20                  25                  30

Ser Lys Val His Asn Glu Val Lys Asn Ile Lys Ile Pro Thr Leu
                35                  40                  45

Val Lys Glu Ser Lys Ile Gln Lys Glu Leu Val Ala Ile Met Asn
                50                  55                  60

Gln His Asp Leu Ile Tyr Thr Tyr Lys Glu Leu Val Gly Thr Gly
                65                  70                  75

Thr Ser Ile Arg Ser Glu Ala Pro Cys Asp Ala Ile Ile Gln Ala
                80                  85                  90

Thr Ile Ala Asp Gln Gly Asn Lys Lys Gly Tyr Ile Asp Asn Trp
                95                  100                 105

Ser Ser Asp Gly Phe Leu Arg Trp Ala His Ala Leu Gly Phe Ile
                110                 115                 120

Glu Tyr Ile Asn Lys Ser Asp Ser Phe Val Ile Thr Asp Val Gly
                125                 130                 135

Leu Ala Tyr Ser Lys Ser Ala Asp Gly Ser Ala Ile Glu Lys Glu
                140                 145                 150

Ile Leu Ile Glu Ala Ile Ser Ser Tyr Pro Pro Ala Ile Arg Ile
                155                 160                 165

Leu Thr Leu Leu Glu Asp Gly Gln His Leu Thr Lys Phe Asp Leu
                170                 175                 180

Gly Lys Asn Leu Gly Phe Ser Gly Glu Ser Gly Phe Thr Ser Leu
```

|     |     |     |     | 185 |     |     |     |     | 190 |     |     |     |     | 195 |     |
| --- | --- | --- | --- | --- | --- | --- | --- | --- | --- | --- | --- | --- | --- | --- | --- |
| Pro | Glu | Gly | Ile | Leu | Leu | Asp | Thr | Leu | Ala | Asn | Ala | Met | Pro | Lys |     |
|     |     |     |     | 200 |     |     |     |     | 205 |     |     |     |     | 210 |     |
| Asp | Lys | Gly | Glu | Ile | Arg | Asn | Asn | Trp | Glu | Gly | Ser | Ser | Asp | Lys |     |
|     |     |     |     | 215 |     |     |     |     | 220 |     |     |     |     | 225 |     |
| Tyr | Ala | Arg | Met | Ile | Gly | Gly | Trp | Leu | Asp | Lys | Leu | Gly | Leu | Val |     |
|     |     |     |     | 230 |     |     |     |     | 235 |     |     |     |     | 240 |     |
| Lys | Gln | Gly | Lys | Lys | Glu | Phe | Ile | Ile | Pro | Thr | Leu | Gly | Lys | Pro |     |
|     |     |     |     | 245 |     |     |     |     | 250 |     |     |     |     | 255 |     |
| Asp | Asn | Lys | Glu | Phe | Ile | Ser | His | Ala | Phe | Lys | Ile | Thr | Gly | Glu |     |
|     |     |     |     | 260 |     |     |     |     | 265 |     |     |     |     | 270 |     |
| Gly | Leu | Lys | Val | Leu | Arg | Arg | Ala | Lys | Gly | Ser | Thr | Lys | Phe | Thr |     |
|     |     |     |     | 275 |     |     |     |     | 280 |     |     |     |     | 285 |     |
| Arg | Val | Pro | Lys | Arg | Val | Tyr | Trp | Glu | Met | Leu | Ala | Thr | Asn | Leu |     |
|     |     |     |     | 290 |     |     |     |     | 295 |     |     |     |     | 300 |     |
| Thr | Asp | Lys | Glu | Tyr | Val | Arg | Thr | Arg | Arg | Ala | Leu | Ile | Leu | Glu |     |
|     |     |     |     | 305 |     |     |     |     | 310 |     |     |     |     | 315 |     |
| Ile | Leu | Ile | Lys | Ala | Gly | Ser | Leu | Lys | Ile | Glu | Gln | Ile | Gln | Asp |     |
|     |     |     |     | 320 |     |     |     |     | 325 |     |     |     |     | 330 |     |
| Asn | Leu | Lys | Lys | Leu | Gly | Phe | Asp | Glu | Val | Ile | Glu | Thr | Ile | Glu |     |
|     |     |     |     | 335 |     |     |     |     | 340 |     |     |     |     | 345 |     |
| Asn | Asp | Ile | Lys | Gly | Leu | Ile | Asn | Thr | Gly | Ile | Phe | Ile | Glu | Ile |     |
|     |     |     |     | 350 |     |     |     |     | 355 |     |     |     |     | 360 |     |
| Lys | Gly | Arg | Phe | Tyr | Gln | Leu | Lys | Asp | His | Ile | Leu | Gln | Phe | Val |     |
|     |     |     |     | 365 |     |     |     |     | 370 |     |     |     |     | 375 |     |
| Ile | Pro | Asn | Arg | Gly | Val | Thr | Lys | Gln | Leu | Val | Lys | Ser | Glu | Leu |     |
|     |     |     |     | 380 |     |     |     |     | 385 |     |     |     |     | 390 |     |
| Glu | Glu | Lys | Lys | Ser | Glu | Leu | Arg | His | Lys | Leu | Lys | Tyr | Val | Pro |     |
|     |     |     |     | 395 |     |     |     |     | 400 |     |     |     |     | 405 |     |
| His | Glu | Tyr | Ile | Glu | Leu | Ile | Glu | Ile | Ala | Arg | Asn | Ser | Thr | Gln |     |
|     |     |     |     | 410 |     |     |     |     | 415 |     |     |     |     | 420 |     |
| Asp | Arg | Ile | Leu | Glu | Met | Lys | Val | Met | Glu | Phe | Phe | Met | Lys | Val |     |
|     |     |     |     | 425 |     |     |     |     | 430 |     |     |     |     | 435 |     |
| Tyr | Gly | Tyr | Arg | Gly | Lys | His | Leu | Gly | Gly | Ser | Arg | Lys | Pro | Asp |     |
|     |     |     |     | 440 |     |     |     |     | 445 |     |     |     |     | 450 |     |
| Gly | Ala | Ile | Tyr | Thr | Val | Gly | Ser | Pro | Ile | Asp | Tyr | Gly | Val | Ile |     |
|     |     |     |     | 455 |     |     |     |     | 460 |     |     |     |     | 465 |     |
| Val | Asp | Thr | Lys | Ala | Tyr | Ser | Gly | Gly | Tyr | Asn | Leu | Pro | Ile | Gly |     |
|     |     |     |     | 470 |     |     |     |     | 475 |     |     |     |     | 480 |     |
| Gln | Ala | Asp | Glu | Met | Gln | Arg | Tyr | Val | Glu | Glu | Asn | Gln | Thr | Arg |     |
|     |     |     |     | 485 |     |     |     |     | 490 |     |     |     |     | 495 |     |
| Asn | Lys | His | Ile | Asn | Pro | Asn | Glu | Trp | Trp | Lys | Val | Tyr | Pro | Ser |     |
|     |     |     |     | 500 |     |     |     |     | 505 |     |     |     |     | 510 |     |
| Ser | Val | Thr | Glu | Phe | Lys | Phe | Leu | Phe | Val | Ser | Gly | His | Phe | Lys |     |
|     |     |     |     | 515 |     |     |     |     | 520 |     |     |     |     | 525 |     |
| Gly | Asn | Tyr | Lys | Ala | Gln | Leu | Thr | Arg | Leu | Asn | His | Ile | Thr | Asn |     |
|     |     |     |     | 530 |     |     |     |     | 535 |     |     |     |     | 540 |     |
| Cys | Asn | Gly | Ala | Val | Leu | Ser | Val | Glu | Glu | Leu | Leu | Ile | Gly | Gly |     |
|     |     |     |     | 545 |     |     |     |     | 550 |     |     |     |     | 555 |     |
| Glu | Met | Ile | Lys | Ala | Gly | Thr | Leu | Thr | Leu | Glu | Glu | Val | Arg | Arg |     |
|     |     |     |     | 560 |     |     |     |     | 565 |     |     |     |     | 570 |     |
| Lys | Phe | Asn | Asn | Gly | Glu | Ile | Asn | Phe |     |     |     |     |     |     |     |
|     |     |     |     | 575 |     |     |     |     |     |     |     |     |     |     |     |

( 2 ) INFORMATION FOR SEQ ID NO:32:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:32:

Lys Gln Leu Val Lys Ser Glu Leu Glu Glu Lys
1               5                   10

( 2 ) INFORMATION FOR SEQ ID NO:33:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

AAGCAACTAG TCAAAAGTGA ACTGGAGGAG AAG                          33

( 2 ) INFORMATION FOR SEQ ID NO:34:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

Leu Val Lys Ser Glu Leu Lys Ser Glu Leu Glu Glu Lys
1               5                   10

( 2 ) INFORMATION FOR SEQ ID NO:35:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

GGACTAGTCA AATCTGAACT TAAAAGTGAA CTGGAGGAGA AG              42

( 2 ) INFORMATION FOR SEQ ID NO:36:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

Leu Val Lys Ser Glu Leu Glu Glu Lys Lys Ser Glu Leu Glu
1               5                   10

Glu Lys
15

( 2 ) INFORMATION FOR SEQ ID NO:37:

( i ) SEQUENCE CHARACTERISTICS:
  ( A ) LENGTH: 51 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:37:

GGACTAGTCA AATCTGAACT TGAGGAGAAG AAAAGTGAAC TGGAGGAGAA G  51

( 2 ) INFORMATION FOR SEQ ID NO:38:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:38:

Asn Phe Xaa Xaa
  1

( 2 ) INFORMATION FOR SEQ ID NO:39:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:39:

TTGAAAATTA CTCCTAGGGG CCCCCCT  27

( 2 ) INFORMATION FOR SEQ ID NO:40:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:40:

GGATGNNNNNNNNNNNNNNNNNN  23

( 2 ) INFORMATION FOR SEQ ID NO:41:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:41:

TACCTGCAGC GGAGGTTTAA AAT ATG CGA AGA CGC GGC CGA  41
                         Met Arg Arg Arg Gly Arg
                         1               5

( 2 ) INFORMATION FOR SEQ ID NO:42:

( i ) SEQUENCE CHARACTERISTICS:
    ( A ) LENGTH: 33 base pairs
    ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:42:

```
T   TAC  TTC  GAC  TTC  TTC  CTC  TAG  GTT  GAT  CAG  AT    33
    Met  Lys  Leu  Lys  Lys  Glu  Ile  Gln  Leu  Val
    1              5                        10
```

( 2 ) INFORMATION FOR SEQ ID NO:43:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:43:

```
CCA  CGG  CAT  ATG  CGA  AGA  CGC  GGC  CGA              27
               Met  Arg  Arg  Arg  Gly  Arg
               1              5
```

( 2 ) INFORMATION FOR SEQ ID NO:44:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:44:

```
TTA  TTG  CCG  CTC  TAT  TTG  AAA  ATT  ACT  CCTAGG  AT   35
Asn  Asn  Gly  Glu  Ile  Asn  Phe
1              5
```

( 2 ) INFORMATION FOR SEQ ID NO:45:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:45:

AGAGGAGGTA ATGGG          15

( 2 ) INFORMATION FOR SEQ ID NO:46:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:46:

ATTAAGGGGG GAAGAG          16

( 2 ) INFORMATION FOR SEQ ID NO:47:

( i ) SEQUENCE CHARACTERISTICS:
( A ) LENGTH: 33 base pairs
( B ) TYPE: nucleic acid

```
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:47:

CTCTAGAGGA  TCCCCGCGCT  TAATGGTTTT  TGC                              3 3

( 2 ) INFORMATION FOR SEQ ID NO:48:

( i ) SEQUENCE CHARACTERISTICS:
         ( A ) LENGTH: 33 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:48:

GAGATCTCCT  AGGGGCGCGA  ATTACCAAAA  ACG                              3 3
```

All publications mentioned hereinabove are hereby incorporated by reference.

While the foregoing invention has been described in some detail for purposes of clarity and understanding, it will be appreciated by one skilled in the art that various changes in form and detail can be made without departing from the true scope of the invention.

What is claimed is:

1. A DNA construct comprising:
   (i) a first DNA segment encoding the catalytic domain of a Type IIS endonuclease which contains the cleavage activity of said Type IIS endonuclease;
   (ii) a second DNA segment encoding a sequence-specific recognition domain other than the recognition domain of said Type IIS endonuclease; and
   (iii) a vector
   wherein said first DNA segment and said second DNA segment are operably linked to said vector so that a single protein is produced.

2. The DNA construct according to claim 1 wherein said Type IIS endonuclease is FokI restriction endonuclease.

3. The DNA construct according to claim 2 wherein said recognition domain is selected from the group consisting of: zinc finger motifs, homeo domain motifs, DNA binding domains of repressors, POU domain motifs (eukaryotic transcription regulators), DNA binding domains of oncogenes and naturally occurring sequence-specific DNA binding proteins that recognize >6 base pairs.

4. The DNA construct according to claim 3 wherein said recognition domain is the homeo domain of Ubx.

5. A procaryotic cell comprising:
   (i) a first DNA segment encoding the catalytic domain of a Type IIS endonuclease which contains the cleavage activity of said Type IIS endonuclease;
   (ii) a second DNA segment encoding a sequence-specific recognition domain other than the recognition domain of said Type IIS endonuclease; and
   (iii) a vector
   wherein said first DNA segment and said second DNA segment are operably linked to said vector so that a single protein is produced.

6. The procaryotic cell of claim 5 wherein said first DNA segment encodes the catalytic domain ($F_N$) of FokI, and said second DNA segment encodes the homeo domain of Ubx.

7. A hybrid restriction enzyme comprising the catalytic domain of a Type IIS endonuclease which contains the cleavage activity of said Type IIS endonuclease covalently linked to a recognition domain other than the recognition domain of said Type IIS endonuclease.

8. The hybrid restriction enzyme of claim 7 wherein said recognition domain, which comprises part of said hybrid restriction enzyme, is selected from the group consisting of: zinc finger motifs, homeo domain motifs, POU domain motifs, DNA binding domains of repressors, DNA binding domains of oncogenes and naturally occurring sequence-specific DNA binding proteins that recognize >6 base pairs.

9. The hybrid restriction enzyme of claim 8 wherein said recognition domain is the homeo domain of Ubx.

10. The hybrid restriction enzyme of claim 9 wherein said Type II endonuclease is FokI restriction endonuclease and said hybrid enzyme is Ubx-$F_N$.

11. A DNA construct comprising:
   (i) a first DNA segment encoding the catalytic domain of a Type IIS endonuclease which contains the cleavage activity of said Type IIS endonuclease;
   (ii) a second DNA segment encoding a sequence-specific recognition domain other than the recognition domain of said Type IIS endonuclease;
   (iii) a third DNA segment comprising one or more codons, wherein said third DNA segment is inserted between said first DNA segment and said second DNA segment; and
   (iv) a vector
   wherein said first DNA segment, second DNA segment and said third DNA segment are operably linked to said vector so that a single protein is produced.

12. The DNA construct according to claim 11 wherein said Type IIS endonuclease is FokI restriction endonuclease.

13. The DNA construct according to claim 12 wherein said third DNA segment consists essentially of four codons.

14. The DNA construct according to claim 13 wherein said four codons of said third DNA segment are inserted at nucleotide 1152 of the gene encoding said endonuclease.

15. The DNA construct according to claim 12 wherein said third DNA segment consists essentially of 7 codons.

16. The DNA construct according to claim 15 wherein said 7 codons of said third DNA segment are inserted at nucleotide 1152 of the gene encoding said endonuclease.

17. The DNA construct according to claim 12 wherein said recognition domain is selected from the group consisting of: zinc finger motifs, homeo domain motifs, POU domain motifs, DNA binding domains of repressors, DNA binding domains of oncogenes and naturally occurring sequence-specific DNA binding proteins that recognize >6 base pairs.

18. A procaryotic cell comprising:
(i) a first DNA segment encoding the catalytic domain of a Type IIS endonuclease which contains the cleavage activity of said Type IIS endonuclease;
(ii) a second DNA segment encoding a sequence-specific recognition domain other than the recognition domain of said Type IIS endonuclease;
(iii) a third DNA segment comprising one or more codons, wherein said third DNA segment is inserted between said first DNA segment and said second DNA segment; and
(iv) a vector
wherein said first DNA segment, said second DNA segment, and said third DNA segment are operably linked to said vector so that a single protein is produced.

19. The procaryotic cell of claim 18 wherein said third DNA segment consists essentially of four codons.

20. The procaryotic cell of claim 18 wherein said third DNA segment consists essentially of seven codons.

21. An isolated hybrid Type IIS endonuclease produced by the procaryotic cell of claim 18.

* * * * *